United States Patent
Fisher et al.

(10) Patent No.: US 9,603,538 B2
(45) Date of Patent: Mar. 28, 2017

(54) IMPLANTABLE CUFF AND METHOD FOR FUNCTIONAL ELECTRICAL STIMULATION AND MONITORING

(71) Applicant: Case Western Reserve University, Cleveland, OH (US)

(72) Inventors: Lee Fisher, Pittsburg, PA (US); Matthew Stone, Strongsville, OH (US); Dustin J. Tyler, Highland Heights, OH (US); Daniel Tan, Cleveland, OH (US); Matthew Schiefer, Shaker Heights, OH (US); Natalie Brill, Lakewood, OH (US); Michael Miller, Cleveland, OH (US); Ronald Triolo, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 231 days.

(21) Appl. No.: 14/408,011

(22) PCT Filed: Jun. 17, 2013

(86) PCT No.: PCT/US2013/046125
§ 371 (c)(1),
(2) Date: Dec. 15, 2014

(87) PCT Pub. No.: WO2013/188871
PCT Pub. Date: Dec. 19, 2013

(65) Prior Publication Data
US 2015/0174396 A1    Jun. 25, 2015

Related U.S. Application Data

(60) Provisional application No. 61/660,353, filed on Jun. 15, 2012.

(51) Int. Cl.
| | | |
|---|---|---|
| *A61B 5/04* | (2006.01) | |
| *A61N 1/05* | (2006.01) | |
| *A61N 1/36* | (2006.01) | |

(52) U.S. Cl.
CPC ........ *A61B 5/04001* (2013.01); *A61N 1/0556* (2013.01); *A61N 1/3605* (2013.01)

(58) Field of Classification Search
CPC .......................... A61B 5/04001; A61N 1/0556
(Continued)

(56) References Cited

U.S. PATENT DOCUMENTS

| | | |
|---|---|---|
| 5,634,462 A | 6/1997 | Tyler et al. |
| 5,938,596 A | 8/1999 | Woloszko et al. |

(Continued)

OTHER PUBLICATIONS

International Search Report for PCT/US2013/046125, mailed Sep. 20, 2013, pp. 1-5.

*Primary Examiner* — Lee S Cohen
(74) *Attorney, Agent, or Firm* — Tarolli, Sundheim, Covell & Tummino LLP

(57) ABSTRACT

An implantable cuff includes an elastic collar, at least one conductive segment disposed on or within the elastic collar, and at least one conductor in electrical communication with the at least one conductive segment. The elastic collar defines an internal opening configured to receive an internal body tissue. At least a portion of the elastic collar includes a stiffening region having a stiffness greater than a second region of the elastic collar. The at least one conductor is configured to operably mate with an apparatus capable of delivering electrical stimulation to, and/or recording an electrical activity of, the internal body tissue.

18 Claims, 20 Drawing Sheets

(58) Field of Classification Search
USPC .......................................... 600/377; 607/118
See application file for complete search history.

(56) References Cited

U.S. PATENT DOCUMENTS

| | | | |
|---|---|---|---|
| 6,308,105 B1 | 10/2001 | Duysens et al. | |
| 6,456,866 B1 | 9/2002 | Tyler et al. | |
| 6,600,956 B2* | 7/2003 | Maschino | A61N 1/0556 607/118 |
| 8,751,017 B2* | 6/2014 | Wilson | A61N 1/0556 607/118 |
| 9,037,248 B2* | 5/2015 | Durand | A61N 1/36071 607/118 |
| 2003/0040785 A1 | 2/2003 | Maschino et al. | |
| 2008/0172116 A1 | 7/2008 | Mrva et al. | |

* cited by examiner

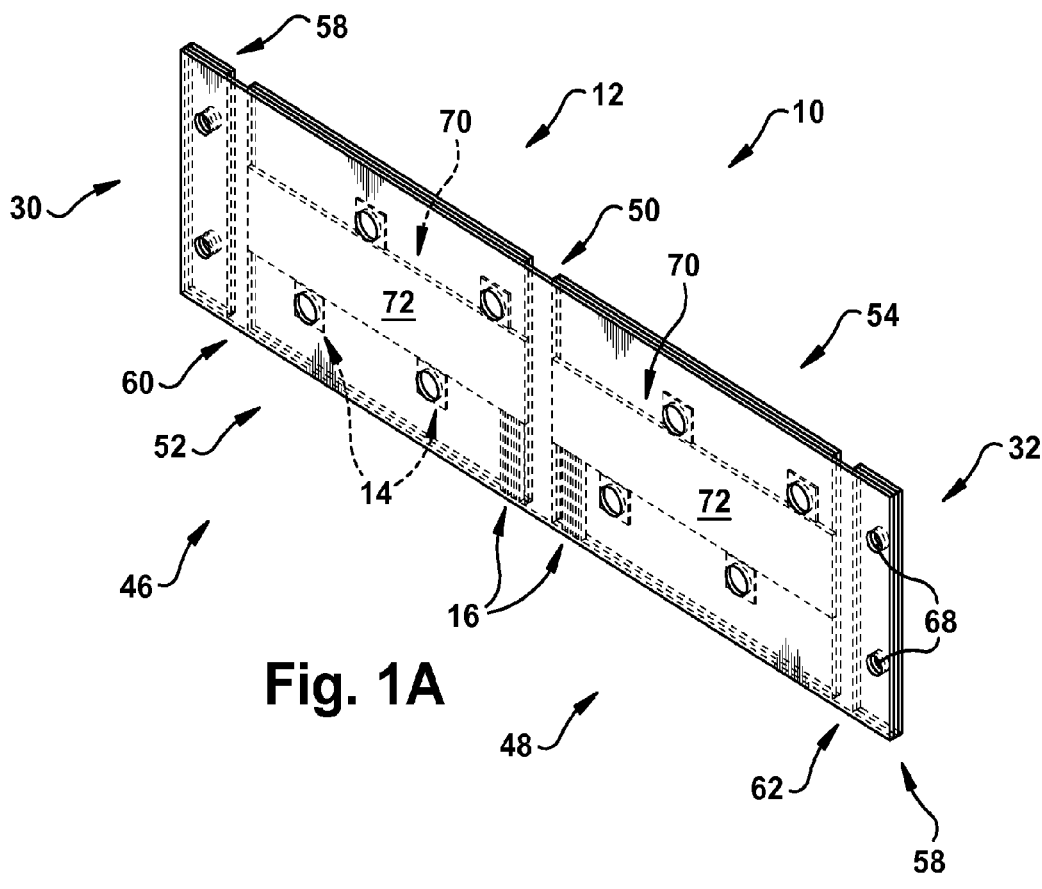
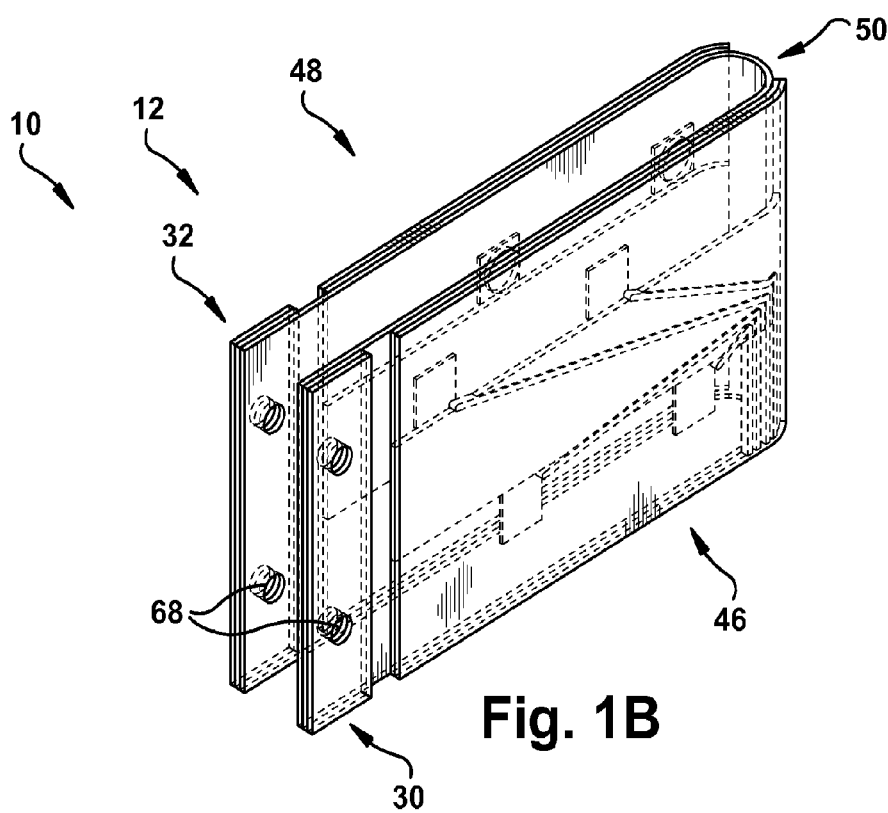

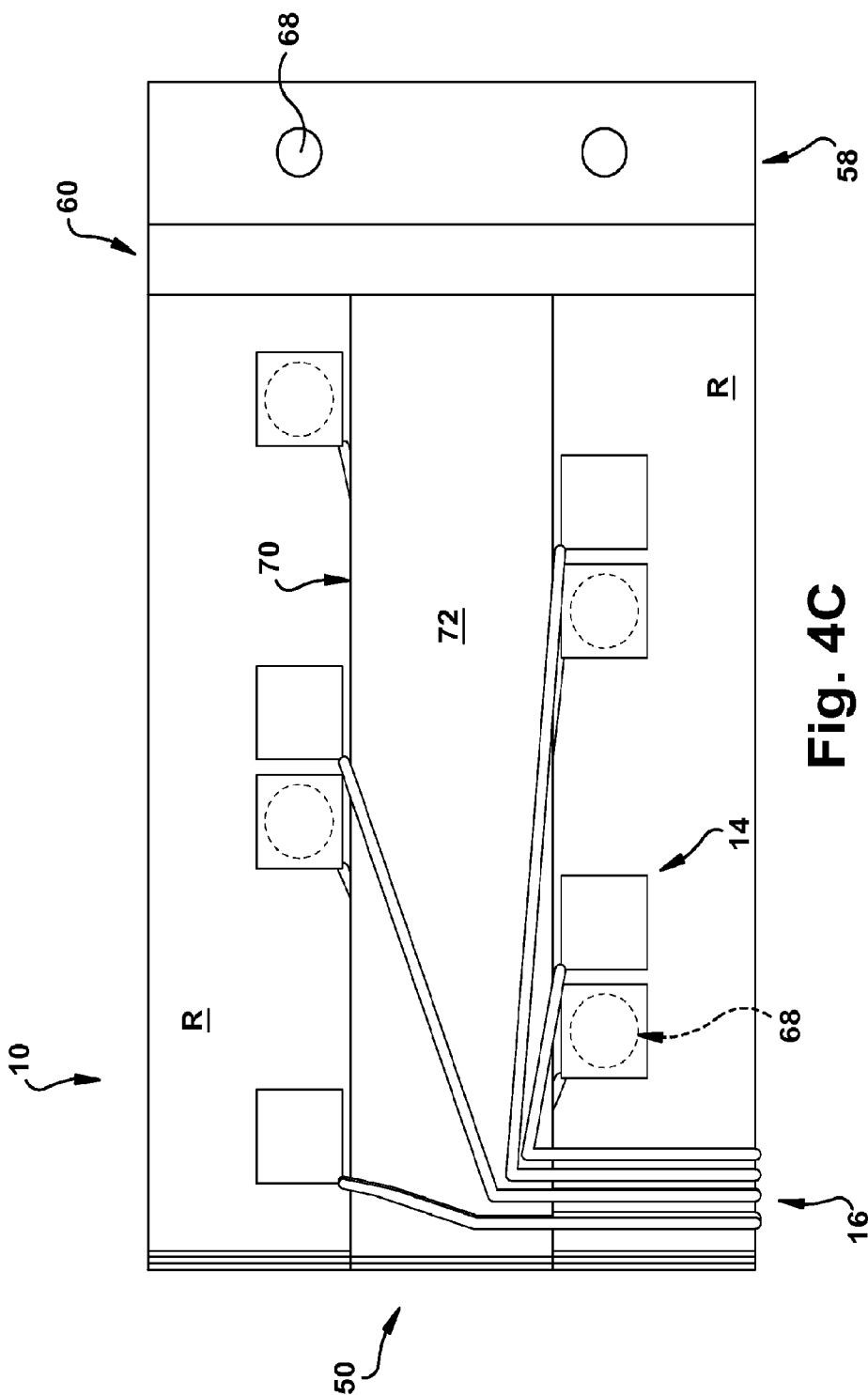

IMPLANTABLE CUFF AND METHOD FOR FUNCTIONAL ELECTRICAL STIMULATION AND MONITORING

RELATED APPLICATION

This application claims the benefit of U.S. Provisional Patent Application Ser. No. 61/660,353, filed Jun. 15, 2012, the entirety of which is hereby incorporated by reference for all purposes.

TECHNICAL FIELD

The present disclosure relates generally to implantable biomedical interfaces, and more particularly to an implantable cuff for biological soft tissue that can be used as an electrode interface for selective stimulation and/or monitoring of nerve groups.

BACKGROUND

As the level of sophistication has increased in biomedical arts, advances have been made in implantable therapies. Therapies have evolved that involve the precise application of stimulus including electrical stimulus medication. Functional electrical stimulation of the nervous system, for example, can be used to help to restore or maintain some degree of lost sensory and motor function in neurologically impaired individuals. In addition, there are certain specialized applications, such as the treatment of sleep apnea and natural interfaces to amputee prosthesis, where it is necessary to simultaneously monitor and generate electrical and chemical signals in nerves. To this end, various implantable devices have been developed for delivering electrical stimulation to peripheral nerves to influence nerve function.

Several types of nerve cuff electrodes are commercially available. Conventional cuff electrodes, for example, include proximity electrodes that are sutured into position. These electrodes require a relatively high amount of current. Half cuff electrodes are generally C-shaped, while cylindrical electrodes can be spiral, helical, split-cylinder, or chambered cylinders. C-shaped or split cylinder electrodes generally include a cylinder of dielectric material with a bore having sufficient diameter to receive a nerve trunk. Single or multiple annular electrodes can be positioned on the inner surface of the bore for applying electrical stimuli. The electrical stimuli, for example, may be used to provide functional electrical stimulation, to block neural nerve impulses traveling along the nerve trunk, or to cause other effects.

The spiral type of cuff electrode typically includes a self-curling sheet of non-conductive material biased-curl into a spiral. Conductive strips or pads are disposed on the self-curling sheet extending peripherally around the inner surface of the cuff. The conductive segments may be electrically conductive for applying electrical impulses, or fluid conductive for infusing or extracting medications. In use, a first edge of a self-curling sheet may be disposed adjacent a nerve truck around which the cuff is positioned. The self-curling sheet is permitted to curl around the nerve forming an annular cuff. Helical electrodes wind around the nerve like a spring, allowing nerve flex and fluid exchange with surrounding tissue.

Another approach to electrical stimulation of the nervous system involves small wire electrodes, which penetrate the perineurium membrane and are advanced into a fascicle of the nerve within fascicular endoneurium. This method is highly invasive.

SUMMARY

One aspect of the present disclosure includes an implantable cuff comprising an elastic collar, at least one conductive segment disposed on or within the elastic collar, and at least one conductor in electrical communication with the at least one conductive segment. The elastic collar defines an internal opening configured to receive an internal body tissue. At least a portion of the elastic collar includes a stiffening region having a stiffness greater than a second region of the elastic collar. The at least one conductor is configured to operably mate with an apparatus capable of delivering electrical stimulation to, and/or monitoring an electrical activity of, the internal body tissue.

Another aspect of the present disclosure includes a method of functional electrical stimulation and/or monitoring of an internal body tissue. One step of the method includes providing an implantable cuff. The implantable cuff includes an elastic collar having at least one stiffening region, at least one conductive segment disposed on or within the elastic collar, and at least one conductor in electrical communication with the at least one conductive segment. The implantable cuff is placed around the internal body tissue so that a non-circumferential force is applied to the internal body tissue without damaging the tissue. Next, an apparatus is operated to deliver electrical stimulation to, and/or monitor an electrical activity of, the internal body tissue.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1A is a perspective view showing an opened configuration of an implantable cuff constructed in accordance with one aspect of the present disclosure;

FIG. 1B is a perspective view showing the implantable cuff of FIG. 1A in a closed-configuration;

FIG. 4C is a plan view showing the implantable cuff of FIGS. 4A-B in the closed configuration;

DETAILED DESCRIPTION

Figure 2:
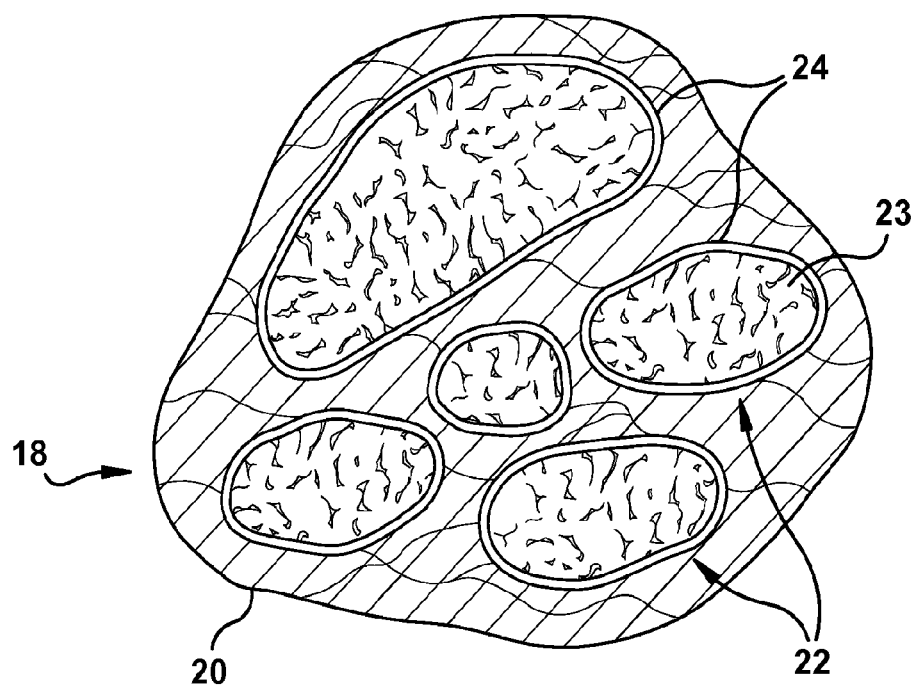
FIG. 2 is a cross-sectional view of a nerve bundle comprised of nerves enclosed within multiple fascicles held together by structural tissue.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "modulate" or "modulating" can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component. In one example, the term "electrical communication" can refer to the ability of an electric field to be transferred to, or have a neuromodulatory effect, within and/or on at least one nerve, neuron, and/or nervous tissue of a subject.

As used herein, the terms "stiff" or "stiffness" can refer to the resistance of an elastic body to deformation by an applied force. The stiffness, k, of a body is a measure of the resistance offered by an elastic body to deformation. For an elastic body with one degree of freedom, for example, the stiffness can be defined as:

$$k = \frac{F}{\delta};$$

where F is the force applied on the body; and where δ is the displacement produced by the force along same degree of freedom.

In this regard, stiffness is not the same as flexural or elastic modulus. For instance, stiffness relates to a property of the solid body whereas flexural or elastic modulus relates to a property of a material of the solid body. Thus, a high modulus of elasticity may be sought when deflection is undesirable, while a low modulus of elasticity may be required when flexibility is needed. (See, e.g., *Handbook of Biomaterials evaluation, Scientific, Technical, and Clinical Testing of Implant Materials*, 2$^{nd}$ edition, edited by Andreas F. von Recum, (1999); and Ratner et al., *Biomaterials Science: An Introduction to Materials in Medicine*, Academic Press (1996)).

As used herein, the terms "flexible" or "flexibility" can refer to the ability of a material or body to deform elastically and return to its original shape when an applied stress is removed.

As used herein, the term "elastic" can refer to the behavior of a material or object, which, when subjected to an applied strain, at least a portion of the material or object extends in the direction of the strain, and when the applied strain is released, the material or object returns (to a degree) to its pre-strained condition.

As used herein, the term "interface" can refer to a point of transfer of information or energy, such as chemical, electrical, force, etc.

The present disclosure relates generally to implantable biomedical interfaces, and more particularly to an implantable cuff for biological soft tissue which can be used as an electrode interface for selective stimulation and/or monitoring of nerve groups. As representative of one aspect of the present disclosure, FIGS. 1A-B illustrate an implantable cuff 10 for functional electrical stimulation and/or monitoring of an internal body tissue. The implantable cuff 10 presents several advantages over conventional electrode cuffs including, but not limited to, the fact that: (1) the design of the implantable cuff allows the cuff to easily wrap into an elongated cross-section around a target body tissue, while minimizing the volume of the implantable cuff and decreasing the risk of nerve compression-related injury; (2) the design and manufacturing process of the implantable cuff offer a high degree of compatibility with microfabrication techniques, which allow for greatly increased electrode contact density; (3) certain regions of the implantable cuff are configured to be highly flexible while other regions are configured to be more inflexible (or stiffer), thereby permitting a wide array of different cuff configurations by changing the size, shape, and materials comprising these regions; and (4) by varying the stiffness in multiple regions of the implantable cuff, the cuff can be selectively configured or tailored to provide different pressure profiles to or within a target tissue.

The body naturally applies small forces to internal body tissues, which result in flattening or other shape changes to the tissues. The present disclosure causes the internal body tissue to mimic its natural reaction to forces applied within the body. More particularly, and as explained in more detail below, the present disclosure is intended to apply a small non-circumferential force over time when implanted about an internal body tissue, which results in a non-damaging pressure within the tissue so as to affect the tissue shape but not so as to occlude or obstruct blood flow within the tissue. In other words, the implantable cuff 10 of the present disclosure can be implanted without damage to the internal body tissue while allowing for tissue swelling and movement.

In one aspect of the present disclosure, the implantable cuff 10 comprises an elastic collar 12, at least one conductive segment 14 disposed on or within the elastic collar, and at least one conductor 16 in electrical communication with the at least one conductive segment. In some instances, the implantable cuff 10 is configured in a similar manner as the cuff disclosed in U.S. Pat. No. 6,456,866 to Tyler et al. (hereinafter, "the '866 patent"), which is hereby incorporated by reference in its entirety. As described in more detail below, the configuration of the implantable cuff 10 can be tailored to a particular desired application. In some instances, for example, the implantable cuff 10 can be specifically configured to stimulate a target internal body tissue. In other instances, the implantable cuff 10 can be specifically configured to record or monitor a physiological parameter of the target internal body tissue. In further instances, the implantable cuff 10 can be specifically configured to both stimulate and record (or monitor) a target internal body tissue. It will be appreciated that the implantable cuff 10 can include a partial or complete controlling circuit or system (e.g., closed-loop) to coordinate stimulation and sensing/recording functions. In any of the aforementioned configurations, the implantable cuff 10 can include a high density of conductive segments 14 (e.g., electrodes 74) capable of stimulating and/or recording (or monitoring) the target internal body tissue.

Reference will be made below to implanting the cuff 10 about a nerve bundle 18, such as the one shown in FIG. 2. In general, a nerve bundle 18 is surrounded by a loose membrane called the epineurium membrane 20. The nerve bundle 18 is typically organized into several groups of axons called fascicles 22. Each fascicle 22 is surrounded by a membrane called the perineurium membrane 24. Within each fascicle 22 is the endoneurium 23, which contains the axons (not shown in detail). It will be appreciated, however, that the cuff 10 (FIGS. 1A-B) can be implanted about internal body tissues other than nerve bundles 18, such as muscle fibers (not shown).

In another aspect, the elastic collar 12 has a band-like shape and is movable from an opened configuration (FIG. 1A) to a closed configuration (FIG. 1B). In the closed configuration, the elastic collar 12 defines an internal opening that is shaped and dimensioned to receive an internal body tissue, such as a nerve bundle 18. Also in the closed configuration, the elastic collar 12 is shaped, dimensioned, and configured to encircle a nerve bundle 18, for example, and gently and non-invasively apply a defined exterior force over time to redefine the geometry of the nerve bundle, such as by flattening. It will be appreciated that the shape change can be in any direction (e.g., radial or axial) along the nerve bundle 18, which may be beneficial for improving the function of the implantable cuff 10.

The elastic collar 12 includes oppositely disposed outer and inner surfaces 26 and 28 that define a thickness T. In some instances, the elastic collar 12 can have a thickness T of about 0.05 mm to about 1.5 mm. In other instances, the elastic collar 12 can have a thickness T of about 0.1 to about 1 mm. In one example, the elastic collar 12 can have a thickness T of about 0.3 mm. In the opened configuration, the elastic collar 12 also includes first and second free ends 30 and 32 that can be brought into contact with one another so as to move the elastic collar into the closed configuration. As described in more detail below, the first and second free ends 30 and 32 can be joined together via an attachment mechanism 34 (FIG. 12), such as a clip or suture to securely wrap the elastic collar 12 around an internal body tissue.

The elastic collar 12 includes a width W and a length L, each of which can be varied depending upon the particular internal body tissue being targeted for implantation. As shown in FIG. 1A, the length L of the elastic collar 12 is less than the width W. It will be appreciated that, in some instances, the length L can be equal to the width W. In other instances, the length L can be greater than the width W. The thickness T, width W, length L, and cross-sectional profile of the elastic collar 12 will determine the magnitude of the force that will be applied to the internal body tissue upon implantation of the cuff 10. And, as discussed in more detail below, the presence and pattern(s) of the stiffening region(s) 70 will determine the magnitude of the force that will be applied to the internal body tissue.

Figure 3A:
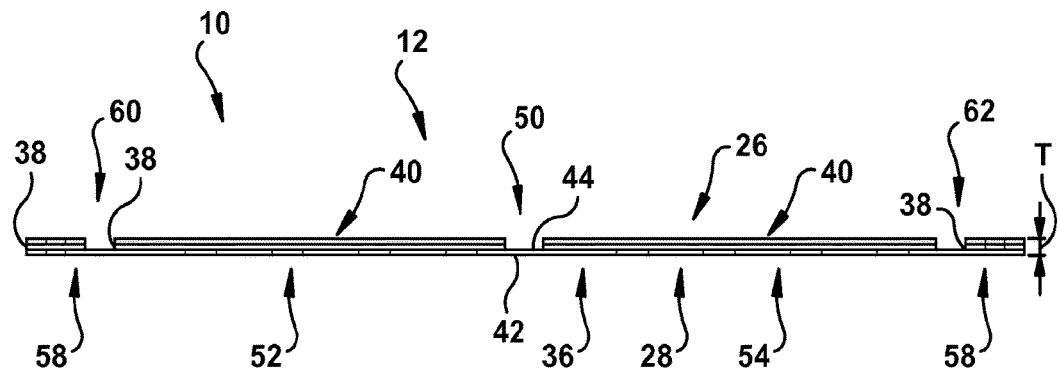
FIG. 3A is a side view of the implantable cuff in FIG. 1A.
Figure 3B:
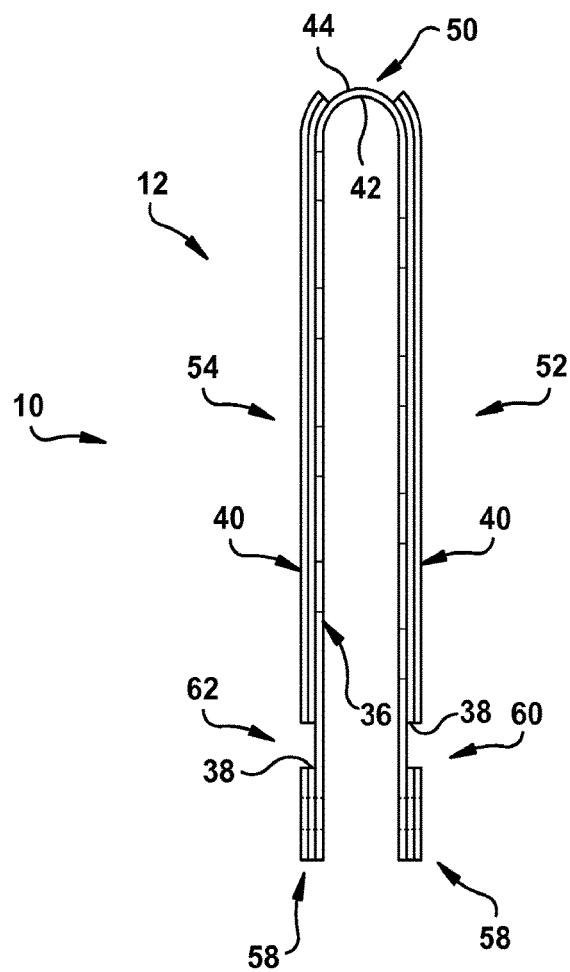
FIG. 3B is a side view of the implantable cuff in FIG. 1B.

In another aspect, the elastic collar 12 has a multi-layered configuration. As shown in FIGS. 3A-B, the elastic collar 12 includes a backing sheet 36, a first non-conductive sheet 38, and a second non-conductive sheet 38. The backing sheet 36 includes oppositely disposed first and second major surfaces 42 and 44. The backing sheet 36 can have a flexible or semi-flexible configuration and be formed, for example, from a biocompatible polymeric material (e.g., a transparent plastic). Each of the first and second non-conductive sheets 38 and 40 can be formed from one or more biocompatible polymeric materials, such as silicone. Each of the first and second non-conductive sheets 38 and 40 can have a thickness of about 0.001 to about 0.009 inches and, for example, about 0.005 inches. The first non-conductive sheet 38 can be sandwiched between the second major surface 44 of the backing sheet 36 and the second non-conductive sheet 40. As described in more detail below, each of the first and second non-conductive sheets 38 and 40 includes a series of non-contiguous portions that define highly flexible regions, which allow the elastic collar 12 to easily bend and wrap around an internal body tissue.

Advantageously, the multi-layer configuration of the elastic collar 12 reduces the volume or bulkiness of the implantable cuff 10. The cuff disclosed in the '866 patent, for example, is manufactured using injection molding techniques. Such techniques provide limited ability to minimize the thickness of the cuff and its components. For example, injection molding techniques limit the thickness of the cuff disclosed in the '866 patent to no less than 1.5 mm. Additionally, the injection molding techniques needed to fabricate the hinge and clasp mechanism of the cuff greatly increase the bulk of the cuff. As a result of this bulkiness, when the cuff of the '866 patent is implanted, there is an increased likelihood that the tissue surrounding cuff will press on the outer walls of the cuff and cause excessive unwanted pressure on the tissue (e.g., the nerve). As compared to the cuff of the '866 patent, the significantly reduced thickness T of the implantable cuff 10 reduces the volume or bulkiness of the elastic collar 12 and thereby decreases the probability of nerve pressure-related adverse events.

In another aspect, the elastic collar 10 (FIGS. 4A-C) comprises oppositely disposed first and second arm members 46 and 48 that are flexibly joined to one another via a hinge region 50. Each of the first and second arm members 46 and 48 also includes first and second tissue contacting portions 52 and 54, respectively, that are spaced apart from one another by the hinge region 50. The hinge region 50 is defined by a portion of the second surface 44 of the backing sheet 36 and a first edge 56 of each of the first and second tissue contacting portions 52 and 54. In some instances, the hinge region 50 has a length Lh that is equal to, or about equal to, the length L of the elastic collar 12. In other instances, the hinge region 50 has a width Wh that can be varied depending, for example, on the dimensions of the internal body tissue. Since the hinge region 50 is essentially a single layer structure (i.e., including a portion of the backing sheet 36), the hinge region is highly flexible as compared to the first and second tissue contacting portions 52 and 54, which allows the elastic collar 12 to easily bend and wrap around an internal body tissue (e.g., a nerve bundle 18).

In another aspect, a distal end portion 58 of each of the first and second arm members 46 and 48 is spaced apart from the first and second tissue contacting portions 52 and 54 by first and second bendable regions 60 and 62, respectively. The first and second bendable regions 60 and 62 are highly flexible (as compared to each of the first and second tissue contacting portions 52 and 54 and the distal end portions 58). The first and second bendable regions 60 and 62 are configured to easily bend and allow the first and second free ends 30 and 32 of the elastic collar 12 to contact one another. Each of the first and second bendable regions 60 and 62 is defined by a portion of the second major surface 44 of the backing sheet 36, as well as a second edge 64 of the first and second tissue contacting portions 52 and 54 (respectively). In some instances, the first and second bendable regions 60 and 62 are similarly or identically configured as the hinge region 50. For instance, each of the first and second bendable regions 60 and 62 can have a length Lb that is equal to, or about equal to, the length L of the elastic collar 12. In other instances, each of the first and second bendable regions 60 and 62 can have a width Wb that is less than, equal to, or greater than the width Wh of the hinge region 50.

Figure 5A:
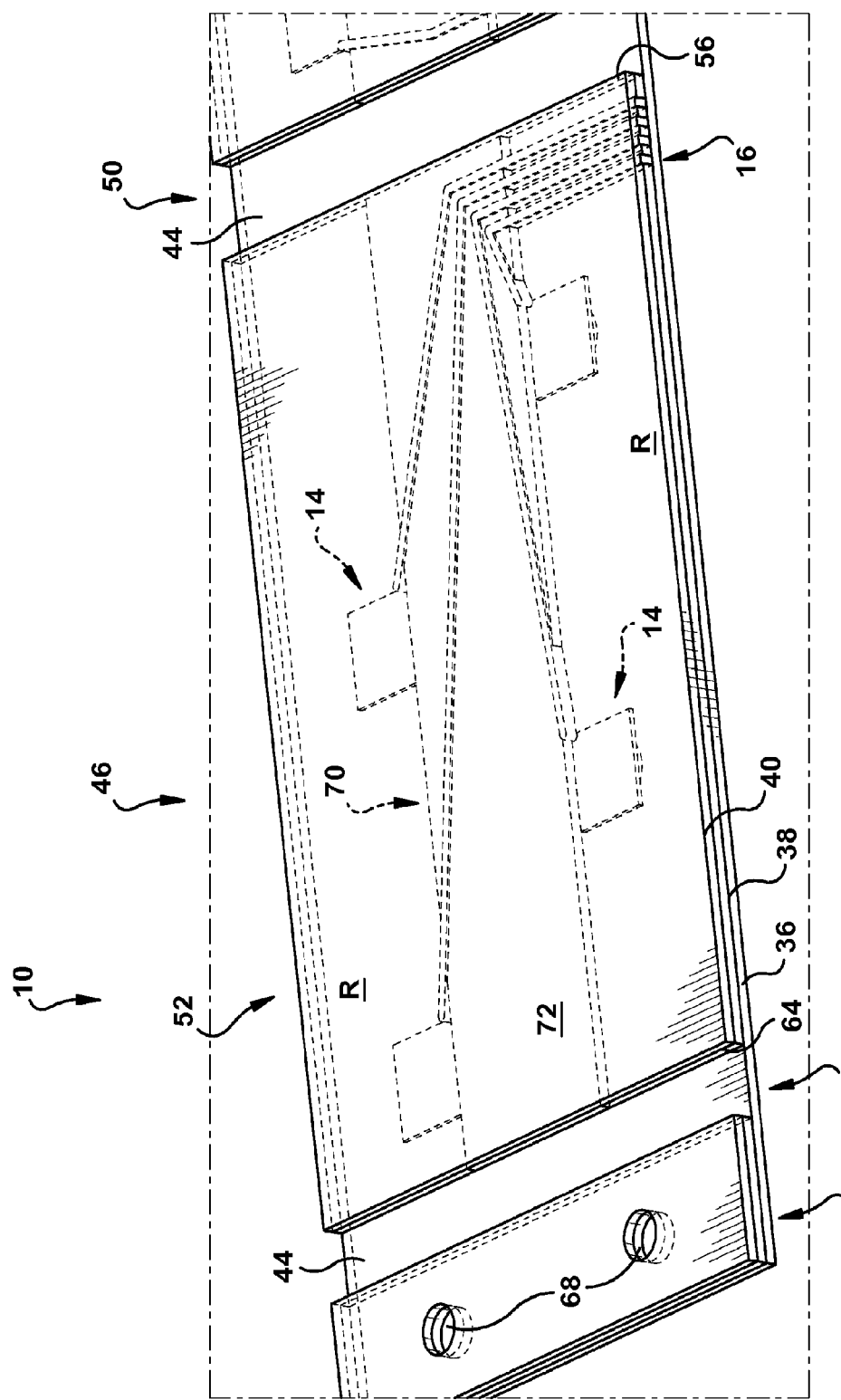
FIG. 5A is a perspective view showing a portion of the implantable cuff in FIGS. 1A-B.
Figure 5B:
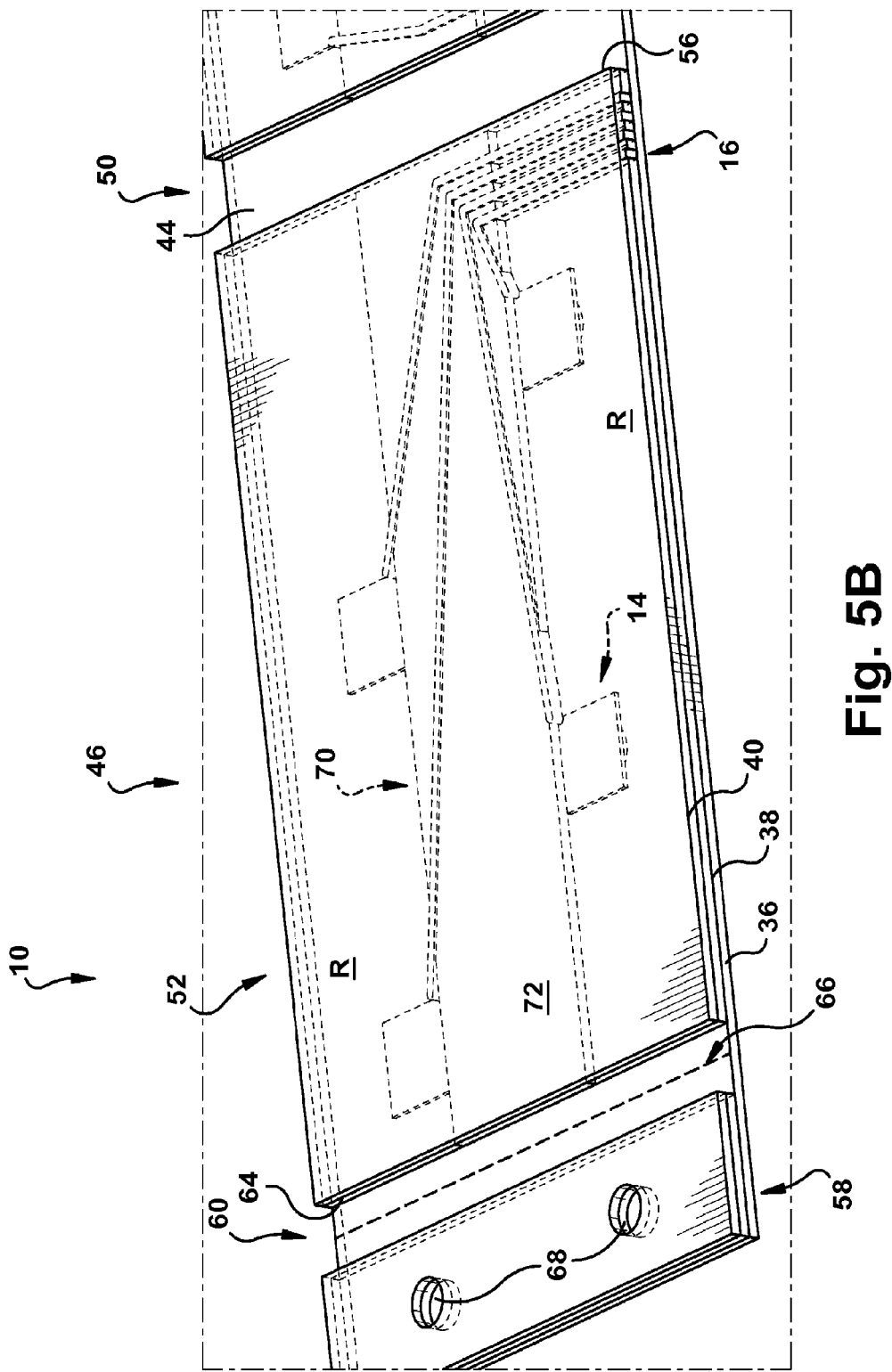
FIG. 5B is a perspective view showing an alternative configuration of the implantable cuff in FIG. 5A.

An alternative configuration of a bendable region 60 and 62, which includes a fail-safe mechanism, is shown in FIG. 5B. When foreign bodies are implanted in humans, the body often responds with inflammation, swelling, and infiltration by additional granulation tissue. These effects can cause the amount of tissue encompassed by a nerve cuff (or other similar device) to increase. In some cases, such swelling and increased accumulation of granulation tissue can produce lasting nerve damage. Advantageously, one aspect of the present disclosure includes a fail-safe mechanism for ensuring that the implantable cuff 10 can be released from about an internal body tissue (e.g., a nerve bundle 18) to relieve potentially damaging pressure build-up caused by inflammation. To this end, one or both of the first and second bendable regions 60 and 62 can include a weakened section 66 configured to tear at a pre-determined pressure of the elastic collar 12. In some instances, the weakened section 66 can include at least one perforated line (e.g., produced by fine laser cutting) that extends across the entire length Lb of one or both of the bendable regions 60 and 62. In the event that inflammation occurs at the implantation site, the perforated line (or lines) can tear at a pre-determined internal pressure of the elastic collar 12 and thereby release the implantable cuff 10 from about the internal body tissue to avoid lasting tissue damage.

Referring again to FIGS. 4A-C, each distal end portion 58 of the first and second arm members 46 and 48 has a multi-layered configuration. In some instances, each distal end portion 58 is comprised of a portion of the first non-conductive sheet 38, which is sandwiched between a portion of the backing sheet 36 and a portion of the second non-conductive sheet 40. Each distal end portion 58 includes a length Ld that can be equal to, or about equal to, the length L of the elastic collar 12. Additionally, each distal end portion 58 includes a width Wd that can be less than, equal to, or greater than the width Wb of the bendable regions 60 and 62. Each distal end portion 58 has a stiffness that is greater than the stiffness of the adjacent bendable region 60 and 62.

Each of the distal end portions 58 also includes at least one opening or channel 68 that extends between the inner and outer surfaces 28 and 26 of the elastic collar 12. In some instances, the opening or channel 68 is configured to receive an attachment mechanism 34, such as a clip, suture, clasp, O-ring, or the like. As described in more detail below, a suture can be passed through an opening or channel 68 of each of the distal end portions 58 to secure the implantable cuff 10 about an internal body tissue. The at least one opening or channel 68 can have a circular cross-sectional profile, an ovoid cross-sectional profile, or any other cross-sectional profile sufficient to receive an attachment mechanism 34. Although each of the distal end portions 58 is illustrated as having two openings or channels 68, it will be appreciated that any number of openings and overlap configurations can be included as part of each distal end portion.

In another aspect, the implantable cuff 10 can include one or more stiffening regions 70 having a stiffness greater than a second region (or regions) of the elastic collar 12. The presence of one or more stiffening regions 70 means that the implantable cuff 10 can be easily tailored to have patternable stiffness; that is, certain regions of the elastic collar 12 can be configured to be highly flexible, while other regions of the elastic collar are configured to be less flexible. The flexible regions allow the elastic collar 12 to bend easily and wrap around an internal body tissue, while the stiffening regions 70 allow the elastic collar to maintain an ovoid cross-sectional shape. By changing the size, shape, and material composition of the stiffening region(s) 70, a wide array implantable cuff configurations with different spatial stiffness distributions are possible. As described in more detail below, the stiffening regions 70 can be arranged in a variety of configurations (e.g., serpentine, checkered, grid-like, etc.) depending upon the intended application of the implantable cuff 10.

In another aspect, one or both of the first and second arm members 46 and 48 includes a stiffening region 70. In some instances, a stiffening region 70 can be comprised of one or more stiffening members 72. In other instances, a stiffening member 72 can be comprised of a material having a modulus of elasticity that is greater than the modulus of elasticity of an adjacent material comprising the elastic collar 12. In one example, a stiffening member 72 can be formed from a biocompatible polymeric material, such as poly ether ketone (PEEK) or other material having a high flexural modulus. Each stiffening member 72 can be disposed on or within the elastic collar 12. In one example, a stiffening member 72 can be disposed between the first and second non-conductive sheets 38 and 40 of the elastic collar 12.

The dimensions of each stiffening member 72 can be varied as needed. In some instances, a stiffening member 72 can have a length Ls that is equal to or less than the length L of the elastic collar 12. In other instances, a stiffening member 72 can have a width Ws that is equal to or less than the width W of the elastic collar 12. In one example, each of the first and second tissue contacting portions 52 and 54 can include a stiffening member 72 having a length Ls that is approximately one-third of the total length L of the elastic collar 12. In this configuration, the adjacent regions R of the first and second tissue contacting portions 52 and 54 (which do not include a stiffening member 72) have a stiffness that is less than the stiffening regions 70, but greater than the stiffness of the hinge region 50 and the bendable regions 60 and 62. The greater stiffness of the adjacent regions R (as compared to the stiffness of the hinge region 50 and the bendable regions 60 and 62) is attributable, at least in part, to their multi-layered configuration, i.e., comprising respective portions of the first and second non-conductive sheets 38 and 40.

The ability to tailor the implantable cuff 10 with different spatial stiffness distributions can result in a tapered, transverse pressure gradient to opposing surfaces of an internal body tissue. When the implantable cuff 10 is implanted about a nerve bundle 18, for example, the areas of the nerve bundle that are not encompassed by the cuff do not experience any transverse pressure, the areas of the nerve bundle beneath the adjacent regions R experience a first degree of pressure, and the areas of the nerve bundle beneath the stiffening regions 70 experience a second degree of pressure that is greater than the first degree of pressure. The tapered, transverse pressure gradient created by the implantable cuff 10 is in contrast to the cuff disclosed in the '866 patent, which does not include regions of varying stiffness and therefore imparts uniform pressure across opposing surfaces of the internal body tissue when implanted. Additionally, the ability to tailor the implantable cuff 10 with different spatial stiffness distributions can result in an implantable cuff having a pre-determined pressure profile. Important physiological and anatomical considerations, such as proper maintenance of blood flow, can be taken into account when tailoring the implantable cuff 10 with a particular spatial stiffness distribution.

In another aspect, the implantable cuff 10 includes at least one conductive segment 14 disposed on or within the elastic collar 12. In some instances, a conductive segment 14 can comprise an electrode 74 configured to deliver electrical energy to an internal body tissue and/or monitor (e.g., record) a parameter (e.g., electrical activity) of the internal body tissue. Electrodes 74 may be made of any material capable of conducting electrical energy, such as platinum (e.g., platinum foil), gold (e.g., gold foil), platinum-iridium, electrically conductive polymers, or the like. Where microfabrication techniques are used to form the implantable cuff 10, the conductive segment(s) 14 can comprise microfabricated electrode contacts.

Figure 4A:
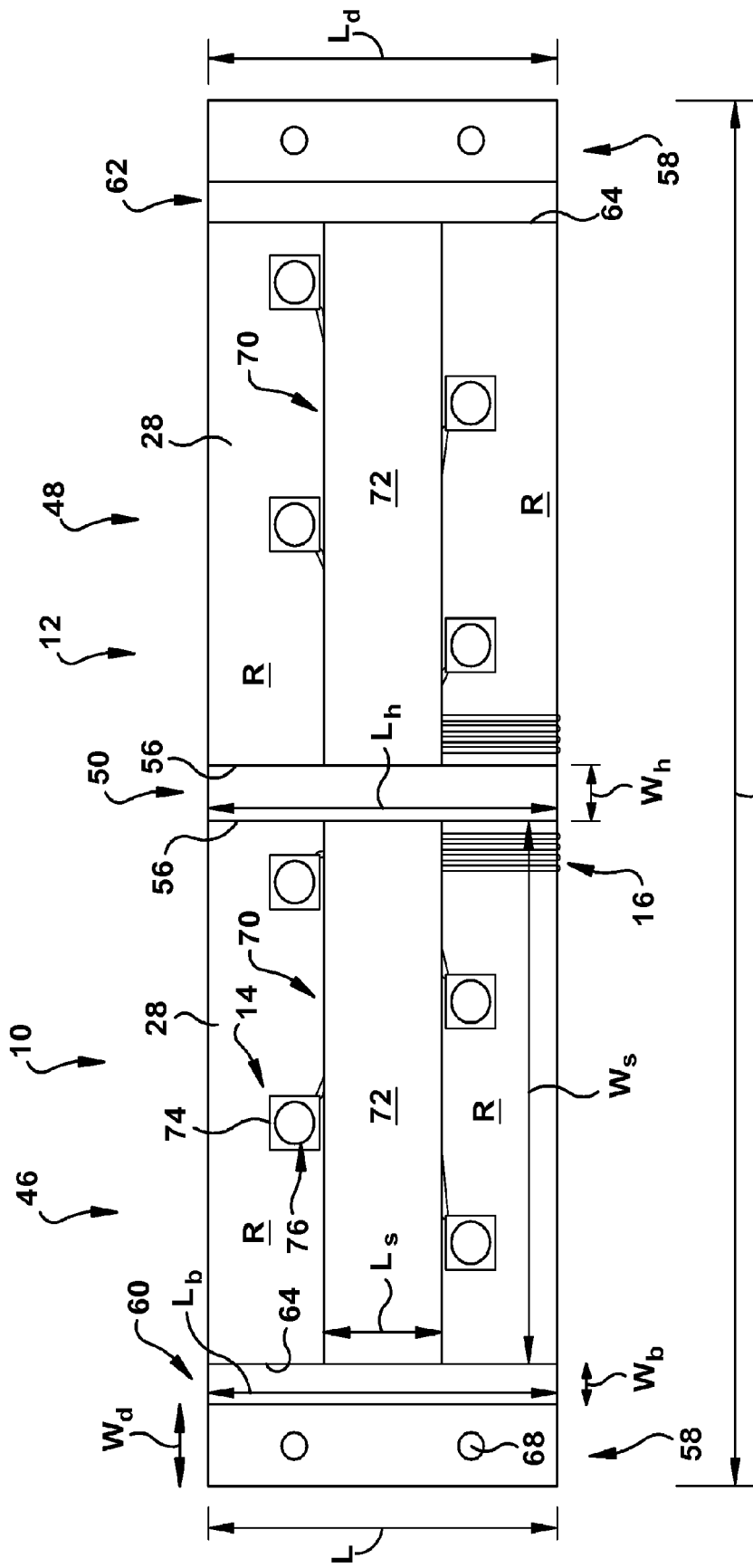
FIG. 4A is a plan view showing an inner surface of the implantable cuff in FIGS. 1A-B.
Figure 4B:
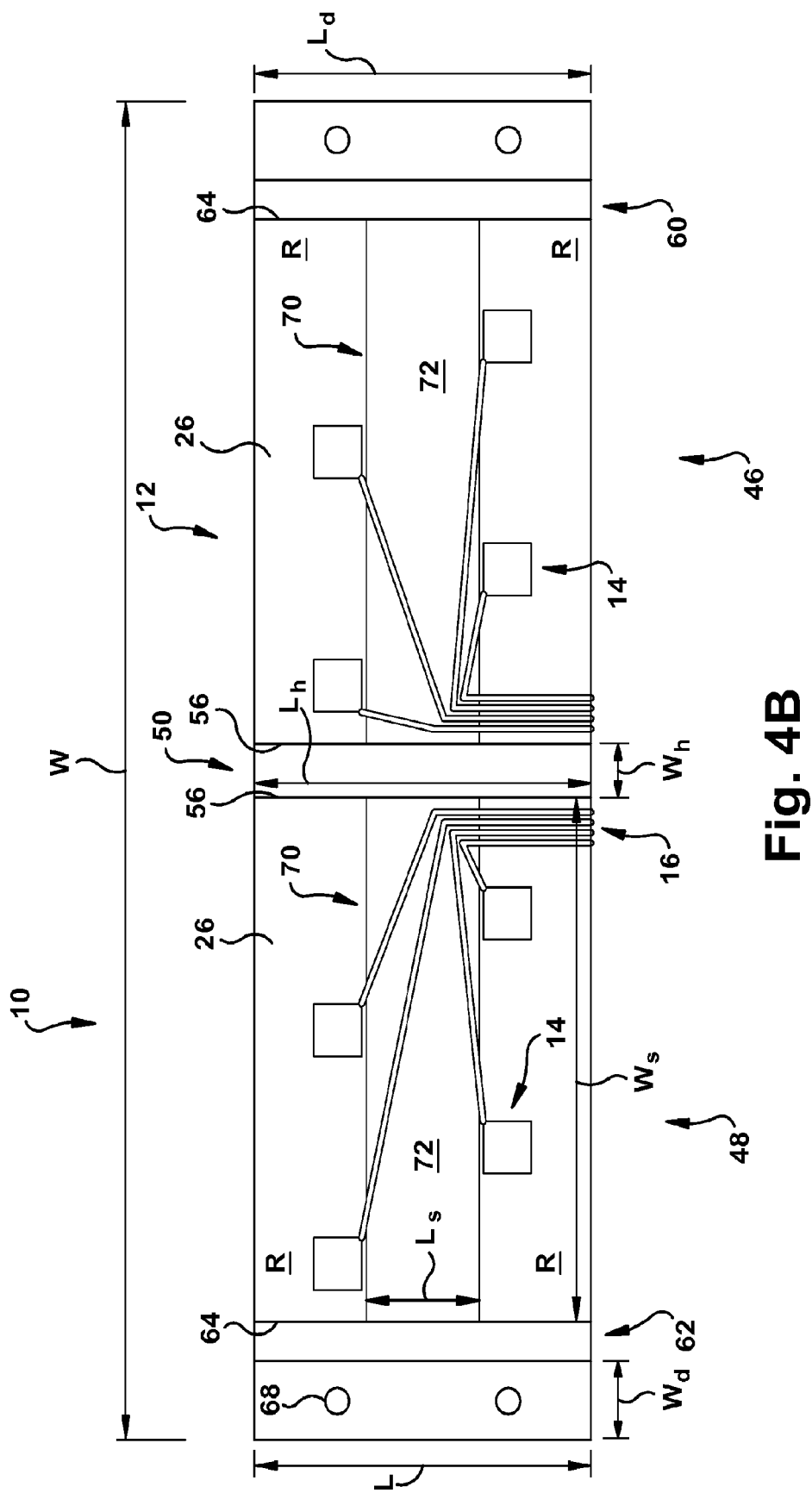
FIG. 4B is a plan view showing an outer surface of the implantable cuff in FIGS. 1A-B.

The implantable cuff 10 can include any desired number of electrodes 74. As shown in FIGS. 4A-B, each of the first and second tissue contacting portions 52 and 54 can include four electrodes 74. The number and position of electrodes 74 can be varied as needed to optimize stimulation and/or monitoring parameters for efficacious therapy delivery and/or diagnostic purposes. The number of electrodes 74, for example, can be determined by the size of the electrodes, the size of the elastic collar 12, and the desired density of the electrodes. The position of the electrodes 74 can be varied depending upon the type of stimulation employed, the anatomy of the target internal body tissue, and the desired energy field. In some instances, electrodes 74 can be disposed between the first and second non-conductive sheets 38 and 40 comprising the first and second tissue contacting portions 52 and 54. To facilitate delivery of electrical energy and/or monitoring, a window or opening 76 may be disposed adjacent each of the conductive segments 14 (e.g., electrodes 74) so as to expose all or only a portion of the conductive segments. In one example, the window or opening 76 can have a circular cross-sectional profile and extend through the second non-conductive sheet 40.

In another aspect, the implantable cuff 10 includes at least one conductor 78 that is in electrical communication with one or more of the conductive segments 14. The conductor(s) 78 is/are configured to operably mate with an apparatus (not shown) capable of delivering electrical stimulation to, and/or monitor an electrical activity of, an internal body tissue. Conductors 78 can be formed from any material capable of conducting electrical energy. In one example, a conductor 78 can include a fine metal wire. As shown in FIG. 4B, each of the electrodes 74 is in direct electrical communication with a separate conductor 78, which extends longitudinally from each electrode to a common exit area within a lead (not shown). There, the lead can extend away from an encircled internal body tissue for subsequent attachment to the operatively associated electrical signal or monitoring device(s).

It will be appreciated that the configuration of the electrode(s) 74 can be varied depending upon the dimensions of the stiffening member(s) 72. For example, microfabricated electrode contacts (and conductors) can be patterned on the stiffening member(s) 72. In this case, a single window or opening 76 adjacent each of the patterned stiffening members 72 can be formed in the second non-conductive sheet 40 so as to expose the electrode contacts. If the stiffening member(s) 72 have difficulty adhering to the first non-conductive sheet 38 and/or the second non-conductive sheet 40, small holes (not shown) can be cut through the stiffening member(s) 72, through which the first non-conductive sheet can bond to the second non-conductive sheet. Such "islands" of the non-conductive sheets 38 and 40 can then serve as plugs to hold the stiffening member(s) 72 in place.

As noted above, one aspect of the present disclosure can include an implantable cuff 10 configured to record (or monitor) a physiological parameter (or parameters) of a target internal body tissue. In one example, the implantable cuff 10 can be configured to record a signal source from a nerve bundle 18. To do so, the implantable cuff 10 can include one or more recording electrodes 74. Additionally or optionally, the implantable cuff 10 can include one or more reference electrodes. The implantable cuff 10 can be configured with reference electrode(s) 74 so as to reduce noise or increase a signal recorded by a recording electrode (or electrodes).

A recording electrode 74 can include any electrode capable of sensing or detecting energy or a signal produced by, or associated with, a nerve bundle 18 (or its constituents). A recording electrode 74 can be comprised of any one or combination of materials capable of generating a change in one or more measurable characteristics in response to the energy or signal produced by, or associated with, a nerve bundle 18. Examples of measurable characteristics can include, but are not limited to, changes in electrical potential, electrical current, optical reflectance, impedance, chemical composition, or the like. The recording electrode(s) 74 can alternatively be configured so that the implantable cuff 10 is capable of measuring a change to an imposed signal resulting from a change in the environment being measured. For example, a recording electrode 74 can measure the changes in current induced during an imposed voltage so that inferences can be made as to the chemical and ionic composition of the constituents surrounding the recording point.

The recording electrode(s) 74 can be configured in a variety of ways to improve the quality of recording. In one example, the implantable cuff 10 can be configured so that one or more recording electrodes 74 extends along a length of a nerve bundle 18 that is greater than the length of a stimulating electrode. In another example, the implantable cuff 10 can be configured so that one or more recording electrodes 74 is/are spaced in a line across the width of the nerve bundle 18. In a further example, the implantable cuff 10 can be configured so that one or more recording electrodes 74 is/are spaced along the length of the nerve bundle (e.g., for conduction velocity measurements) or, alternatively, the recording electrode(s) can have an entirely different distribution that is tailored to the specific location and behavior of the electrical signal(s) of interest.

As also noted above, the implantable cuff 10 can be configured to include one or more regions of high density electrical contacts, such as stimulating electrodes or recording electrodes using one or more microfabrication techniques. A particular high density region can include only stimulating electrodes, only recording electrodes, or a combination thereof. A high density region can cover the entire elastic collar 12 or only a portion thereof. In some instances, the implantable cuff 10 can include a first high density region of stimulating electrodes and an adjacent second high density region of recording electrodes. It will be appreciated that a variety of different high density patterns are possible, depending upon the intended application of the implantable cuff 10.

In some instances, electrode contacts can be patterned onto a biocompatible substrate using a metal deposition microfabrication technique. The substrate for this patterning can comprise the stiffening member 72 already in use in the cuff 10 or, alternatively, the substrate can include an additional layer. The conductors 16 (e.g., metallic traces) patterned on the substrate can be very thin and spaced closely together, which permits the associated electrode contacts (e.g., at the end of these traces) to be very small and densely packed. This configuration allows the size arrangement of the electrode contacts to be easily varied and precisely manufactured.

In other instances, an insulative layer (not shown) can be laid over the conductors 16 and the substrate (e.g., on the inner surface 28 of the elastic collar 12). The insulative layer can be selectively patterned to keep the entirety of the conductors 16 from contacting the associated internal body tissue. The patterned insulative layer ensures that only the intended electrode contact sites contact the internal target issue, and that the conductors 16 are electrically insulated from the tissue.

Once the substrate, the conductors 16 (e.g., metallic traces), and the insulative layer have been fabricated, the entire assembly can be inserted into the elastic collar 12 (e.g., in an intermediate manufacturing step) so that the assembly is held (e.g., encapsulated) inside the elastic collar. Through-holes can be cut in non-stimulating regions of the assembly so that the elastic collar 12 can be formed through the assembly to hold the assembly in place (e.g., on the inner surface 28 of the elastic collar). It will be appreciated that fluid channels (not shown), organic molecules, and/or other energy transfer mechanisms can be patterned (e.g., using lithographic techniques) to produce a dense array of interface or electrode contacts.

Figure 6:
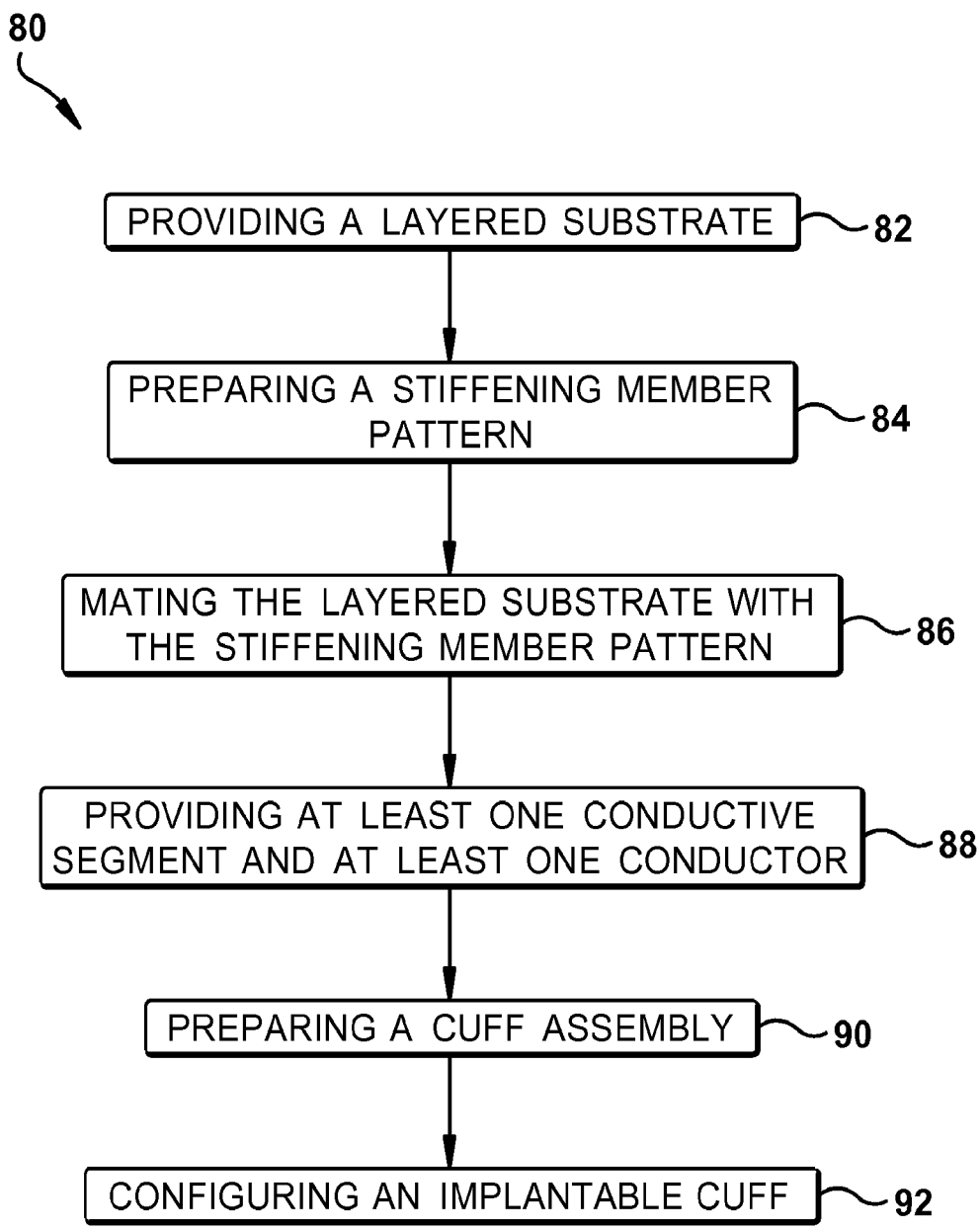
FIG. 6 is a process flow diagram illustrating a method for forming an implantable cuff according to another aspect of the present disclosure.

Another aspect of the present disclosure is illustrated in FIG. 6 and includes a method 80 for forming an implantable cuff 10. Currently, most cuff electrodes use very small wires and hand spot-welded metal foil contacts to deliver an electrical stimulus from an electrical stimulator to an internal body tissue, such as a nerve. Unlike this type of macrofabrication technique, the implantable cuff 10 of the present invention is highly compatible with, and can thus be formed by, microfabrication techniques. The implantable cuff 10 is highly compatible with microfabrication technology because: (1) the multi-layered configuration of the cuff enables easy "sandwiching" of microfabricated electrode contacts and conductors; and (2) the stiffening members 72 used to form the stiffening regions 70 may be comprised of a biocompatible polymer (or polymers), which may be used as the substrate for patterning the electrode contacts and conductors thereon.

Although the method 80 is described below using a macrofabrication technique, it will be appreciated that the technique is merely exemplary and, as discussed above, microfabrication techniques can be used to form the implantable cuff 10. Certain aspects of the method 80 may be identical or similar to the manufacturing method disclosed in U.S. Pat. No. 4,602,624 to Mortimer et al. (hereinafter, "the '624 patent"), the entirety of which is hereby incorporated by reference. At Step 82, for example, a layered substrate is provided in a substantially similar manner as disclosed in the '624 patent. In one example, a thin sheet of silicone (e.g., about 0.005 inch thickness) that is larger than the final dimensions of the implantable cuff 10 is affixed to a flat piece of similarly-sized thin plastic backing (e.g., a transparent material) by static cling forces. This silicone/plastic substrate is then placed plastic-side-down on the center of a stainless steel molding plate so that the stainless steel plate extends past the silicone on all sides. The silicone/plastic substrate is then taped in place.

Next, a sufficient quantity of two-part silicone elastomer is thoroughly mixed and placed into a vacuum chamber. Once a vacuum pump is activated, minute air bubbles trapped in the silicone can "bubble out" of the mixture. When all visible bubbles have left the mixture, the silicone elastomer is placed in a refrigerator until needed. Through this point of the method 80, the fabrication process of the present disclosure is essentially identical to the manufacturing method disclosed in the '624 patent.

At Step 84, a stiffening member pattern is prepared. First, a thin stiffening material (e.g., about 0.005 inch thickness), such as PEEK is cut into the following shapes: a first rectangular piece A, which corresponds to the dimensions of the top side of the stiffening member 72; a second rectangular piece B, which corresponds to the dimensions of the bottom side of the stiffening member; a third rectangular piece C, which corresponds to the dimensions of the hinge region 50; a fourth rectangular piece D, which corresponds to the dimensions of the top side of a distal end portion 58; and a fifth rectangular piece E, which corresponds to the dimensions of the bottom side of the distal end portion.

Figure 7:
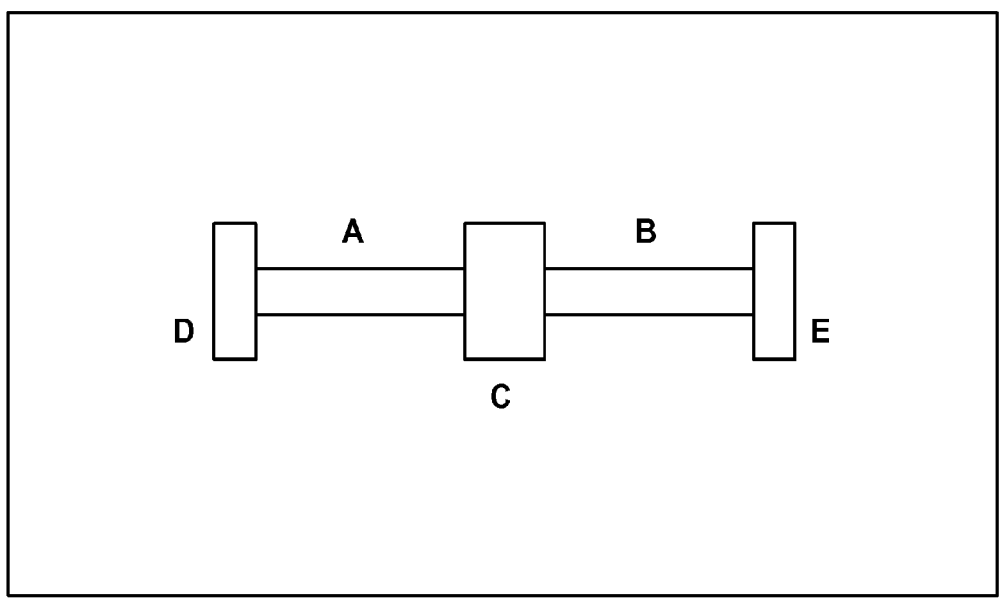
FIG. 7 is a schematic illustration showing the arrangement of pieces A-E used to form the implantable cuff according to one step of the method (FIG. 6)

At Step 86, the two-part silicone adhesive is then used to glue the pieces A-E to the silicone sheeting (FIG. 7). After wiping off any excessive silicone adhesive, the silicone is cured by placing it in an oven. The resultant cuff assembly can then be removed from the oven and cooled. Although rectangular pieces are illustrated in FIG. 7, it will be appreciated that the pieces can have any shape depending upon the desired shape of the stiffening member 72.

At Step 88, at least one conductive segment 14 and at least one conductor 78 are provided. For example, once the cuff assembly is cooled, a silicone adhesive can be used to affix the conductive segment(s) 14 (e.g., electrode contacts) and conductors 78 (e.g., lead wires) of the cuff assembly. The silicone adhesive can then be cured in another oven baking step. Fabrication of the lead wires and electrode contacts involves spot-welding and heat deinsulation. As discussed above, however, it will be appreciated the addition of electrode contacts and lead wires would be unnecessary using microfabricated electrode contacts because the metal contacts and traces would already have been patterned onto pieces A and B of the stiffening member 72.

Figure 8:
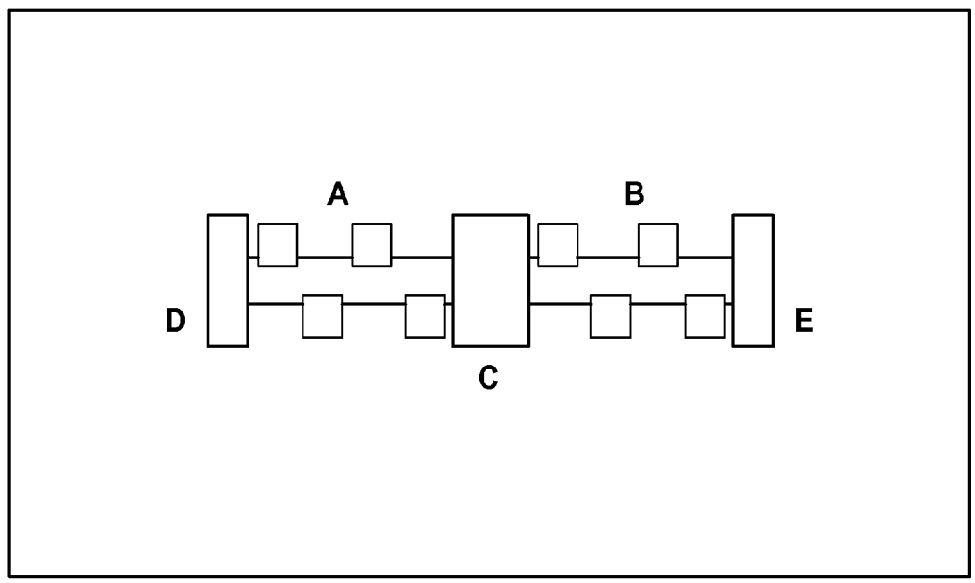
FIG. 8 is a schematic illustration showing the pieces A-E in FIG. 7 arranged with a plurality of electrode contacts.

The cuff assembly is then further prepared at Step 90. To do so, a second sheet of thin silicone sheeting (e.g., about the same size as the first silicone sheet) is affixed to a second piece of thin backing plastic (e.g., about the same size as the first backing plastic) using static cling. A heavy layer of two-part silicone adhesive can then be applied to the electrode assembly. Next, the second silicone sheet/plastic assembly can be placed silicone-side-down onto the electrode assembly. A second stainless steel plate is then placed on top of the electrode assembly, which is then placed in the oven. Approximately 10 lbs. of weight are placed on top of the stainless steel plate to cause any excess silicone to flow away from the electrode assembly. After the electrode assembly has cured, it can be removed from the oven. Once cooled, the top stainless steel plate is removed along with the top layer of backing plastic to yield an electrode assembly having the configuration shown in FIG. 8.

Figure 9:
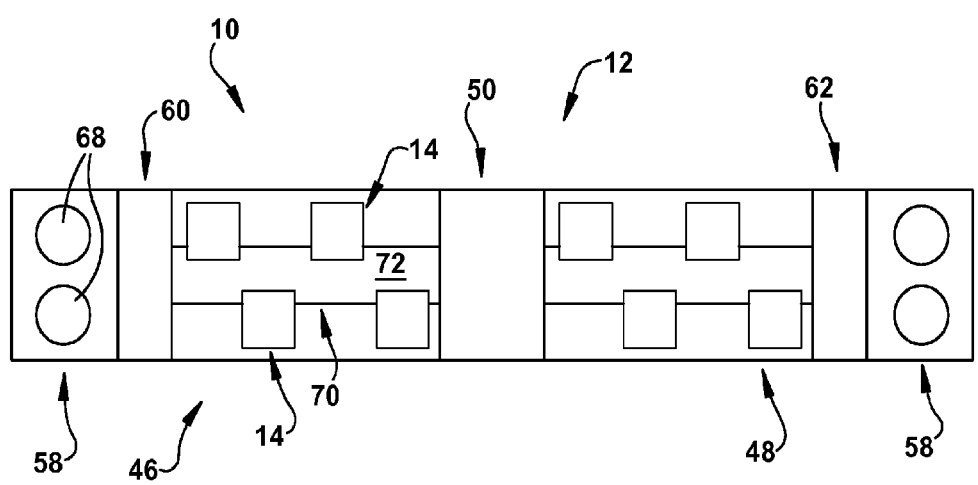
FIG. 9 is a schematic illustration showing an implantable cuff formed according to the method of FIG. 6.

At Step 92, the electrode assembly is shaped and modified to form the implantable cuff 10. Using a scalpel, for example, the rectangular silicone body is cut away and flipped to its reverse side. Only the top layer of silicone on top of the stiffening member 72 is then cut (i.e., pieces C, D and E) are then selectively removed. This will expose pieces C, D and E. Next, pieces C, D, and E are peeled away. In the locations where pieces C, D, and E once were, only the bottom layer of silicone will remain. The purpose of embedding pieces C, D, and E in Step B is to prevent the top and bottom layers of silicone from bonding to each other in these regions. This is how the very flexible regions of the elastic collar 12 (e.g., the hinge region 50 and bendable regions 60 and 62) are formed. Finally, a cylindrical cutting tool (e.g., a hypodermic tube) can be used to punch out contact windows (e.g., through the inside layer of silicone above each of the electrode contacts) so that each electrode contact is exposed. The hypodermic tube can be further used to bore a hole 68 in each of the four suture locations. The resultant implantable cuff 10 is shown in FIG. 9 (leads and contact windows not shown).

Figure 10:
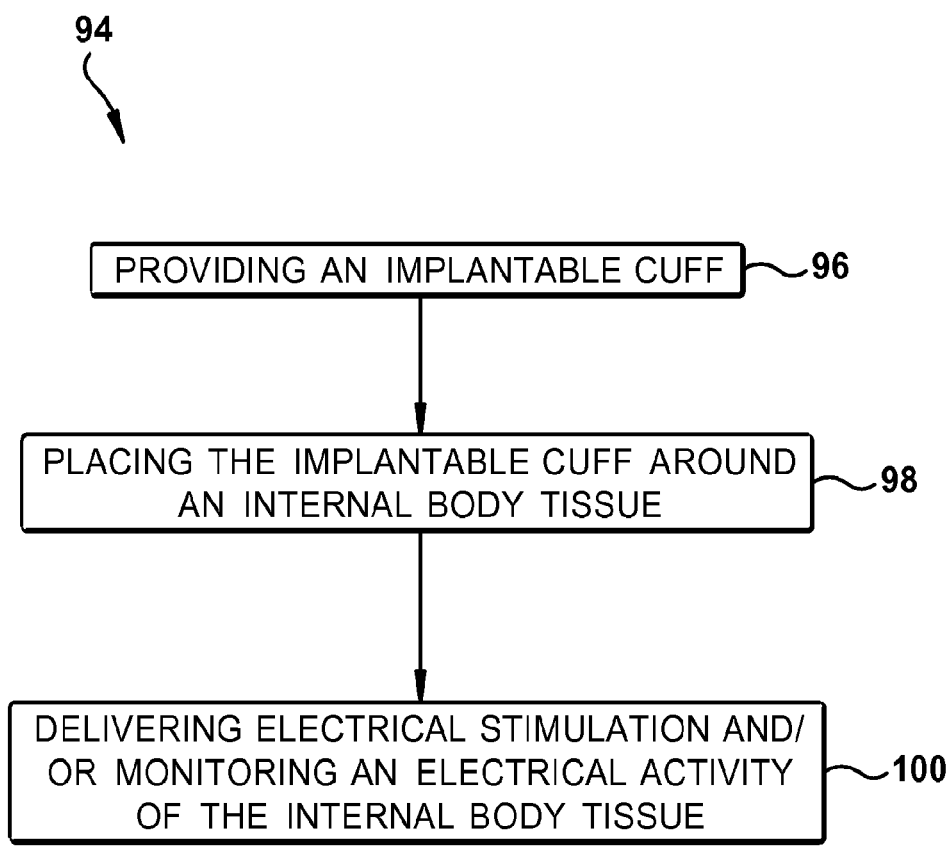
FIG. 10 is a process flow diagram illustrating a method for functional electrical stimulation and/or monitoring of an internal body tissue according to another aspect of the present disclosure.

Another aspect of the present disclosure is illustrated in FIG. 10 and includes a method 94 for functional electrical stimulation and/or monitoring of an internal body tissue. The method 94 is similar to the neuromodulatory method disclosed in the '866 patent, except where as described below. At Step 96 of the method 94, an implantable cuff 10 is provided. The implantable cuff 10 can be identically or similarly constructed as the implantable cuff illustrated in FIGS. 1A-B and described above. For example, the implantable cuff 10 can comprise an elastic collar 12, at least one conductive segment 14 (e.g., a plurality of electrodes 74) disposed on or within the elastic collar, and at least one conductor 78 (e.g., a plurality of thin metal wires) in electrical communication with the at least one conductive segment. The implantable cuff 10 can further comprise a plurality of stiffening regions 70, each of which can include one or more stiffening members 72 made, for example, of PEEK.

Figure 11:
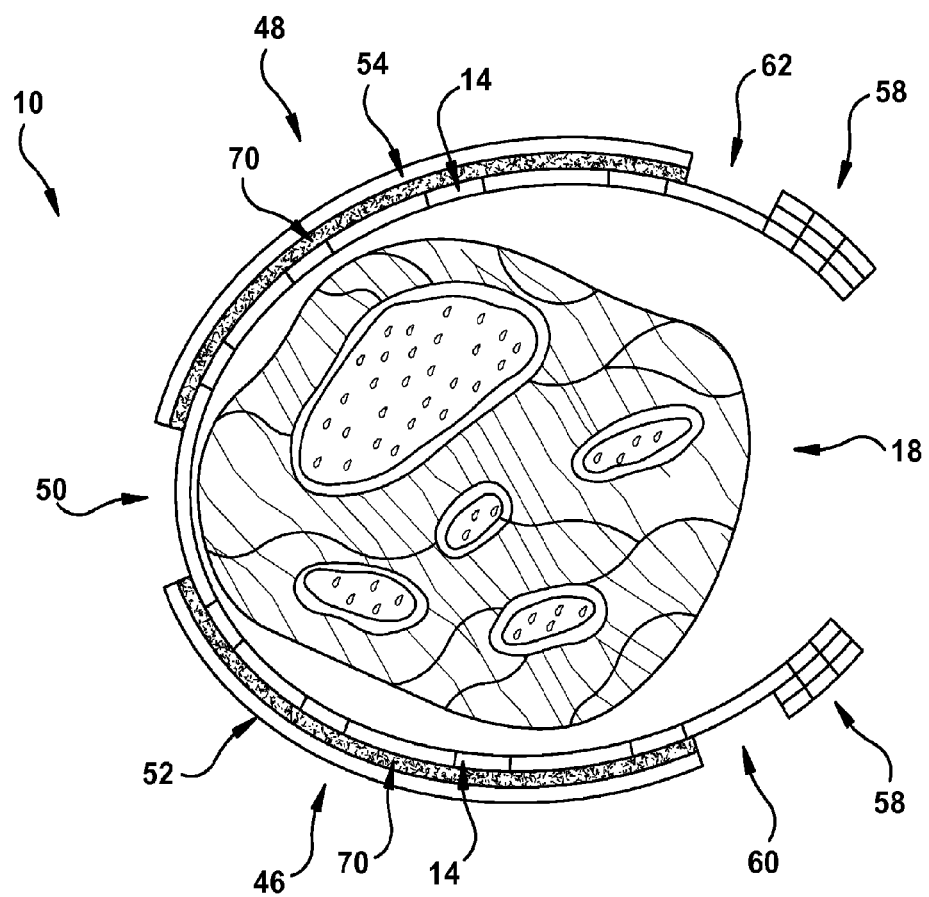
FIG. 11 is a cross-sectional view showing the implantable cuff of FIGS. 1A-B placed about a nerve bundle in an opened configuration.

At Step 98, the implantable cuff 10 is surgically placed around an internal body tissue, such as a nerve bundle 18. An open surgical procedure can be used to place the implantable cuff 10; however, it will be appreciated that minimally invasive and/or percutaneous techniques may additionally or optionally be used. To implant the cuff 10, the cuff is first placed in the open configuration. The first free end 30 of the elastic collar 12 is then positioned about one side of the nerve bundle 18. For example, the cuff 10 can be positioned about the nerve bundle 18 so that the first tissue contacting portion 52 is directly beneath a portion of the nerve bundle (FIG. 11).

Figure 12:
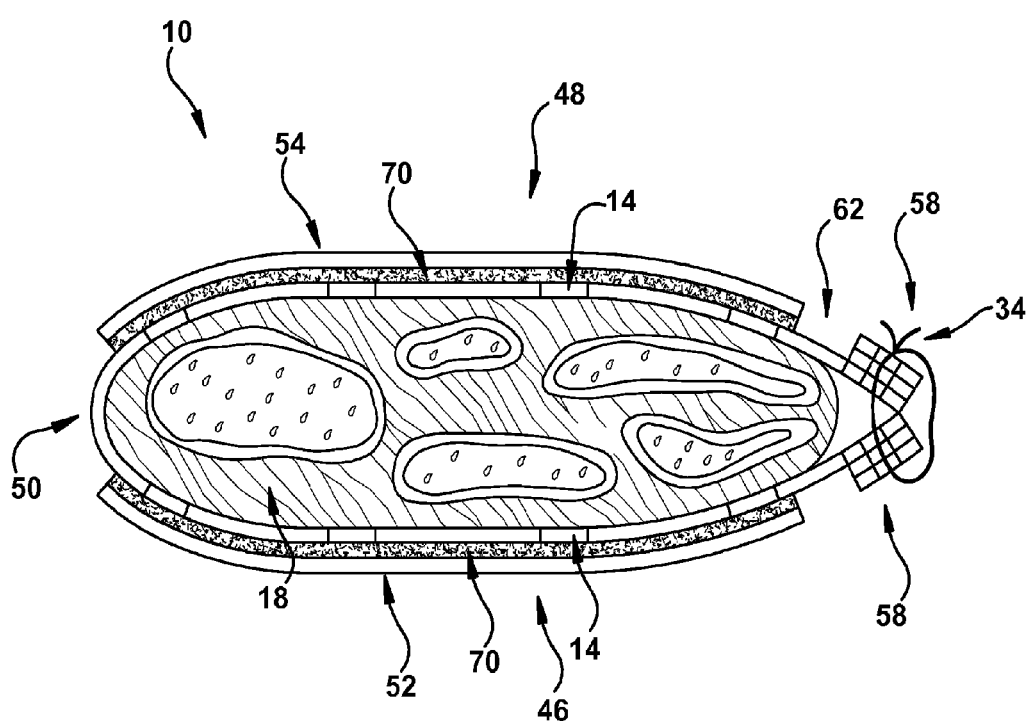
FIG. 12 is a cross-sectional view showing the implantable cuff of FIG. 11 in a closed configuration.

Once the implantable cuff 10 is appropriately positioned about the nerve bundle 18, the cuff is manipulated to move the cuff into the closed positioned. As shown in FIG. 11, for example, the second arm member 48 of the elastic collar 12 can be carefully folded over the uncovered portion of the nerve bundle 18 so that the second tissue contacting portion 54 covers a portion of the nerve bundle. With the implantable cuff 10 wrapped substantially about the nerve bundle 18, the distal end portion 58 of each of the first and second arm members 46 and 48 can be brought into contact with one another. For example, the distal end portions 58 can be contacted with one another so that the openings or channels 68 of each the distal end portions are aligned with one another. Once the openings or channels 68 have been aligned with each other, an attachment mechanism 34 (e.g., a suture) can be passed through each of the openings or channels and tied together to securely attach the implantable cuff 10 about the nerve bundle 18 (FIG. 12).

Contacting the distal end portions 58 with one another causes the nerve bundle 18 to deform from a substantially circular cross-sectional profile to a substantially oval-shaped or flattened cross-sectional profile as result of the transverse pressure applied to opposing surfaces of the nerve bundle by the implantable cuff 10. Application of the cuff 10 spreads the fascicles 22 of the nerve bundle and flattens the epineurium membrane 20 (and ultimately of the perineurium membrane 24 with a corresponding reshaping of the fascicles themselves). This flattening action effectively allows the conductive segments 14 to contact particular fascicles 22 through the epineurium membrane 20 without puncturing either the perineurium membrane 24 or the epineurium. Instead, the fascicles 22 are displaced with a subsequent reshaping of the epineurium membrane 20 at locations corresponding to the cuff interface.

Once the implantable cuff 10 is securely attached to the nerve bundle 18, an apparatus can be operated to deliver electrical stimulation to, and/or monitor an electrical activity of, the nerve bundle. Delivery of electrical stimulation to the conductive elements 14, for example, can result in activation of separate and distinct regions of the nerve bundle 18, along both the longitudinal and radial axis of the nerve bundle. The conductive elements 14 are also capable of sensing small neural signals with better signal-to-noise ratios due to the close proximity of each of the conductive elements to the axons comprising the fascicles 22. In some instances, stimulation and monitoring can be performed simultaneously. In other instances, stimulation and monitoring can be performed intermittently.

Advantageously, for the same cross-sectional area, the circumference of the flattened nerve bundle geometry is larger and thereby allows more conductive elements 14 to be placed around the nerve bundle 18. Additionally, the maximum distance from any axon to a conductive element 14 is smaller than for a circular electrode, effectively moving central tissue to the surface of the nerve bundle 18. Moreover, the flat geometry of the implantable cuff 10 aligns the nerve fascicles 22 to increase selectivity and access to every fascicle.

Figure 13:
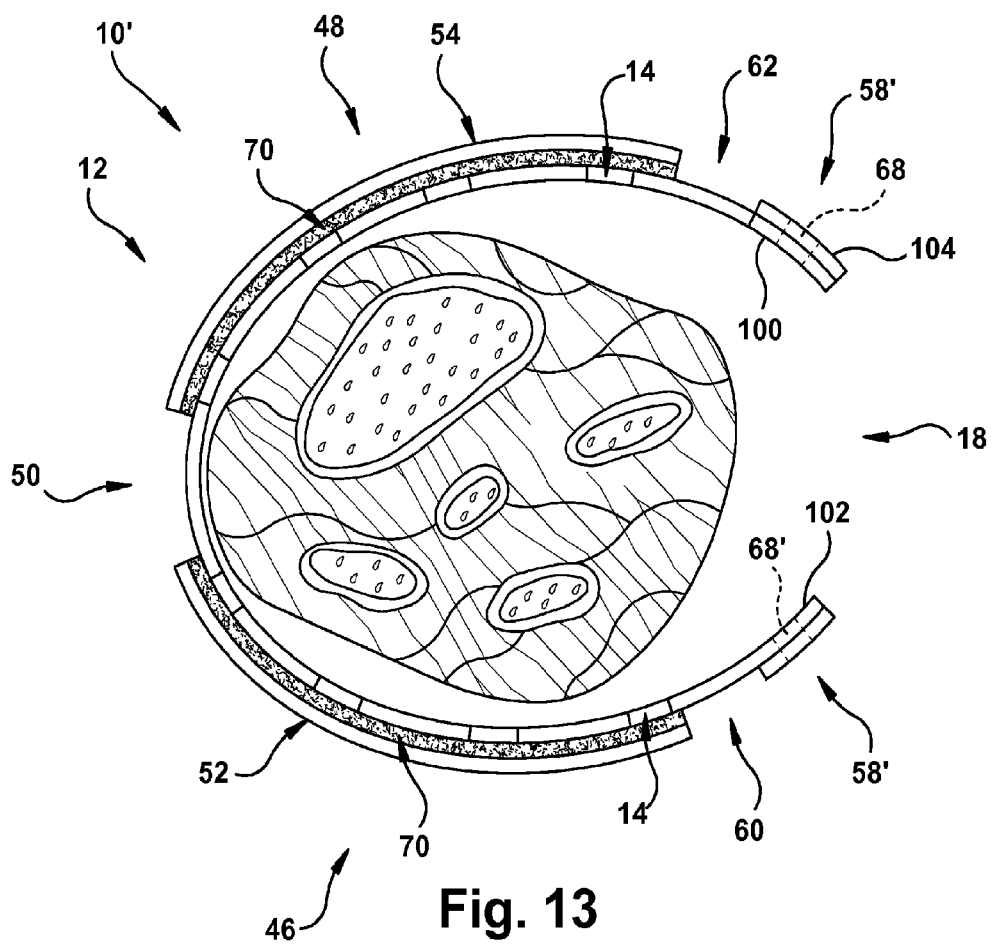
FIG. 13 is a cross-sectional view showing an alternative configuration of the implantable cuff in FIGS. 1A-B placed about a nerve bundle in an opened configuration.
Figure 14:
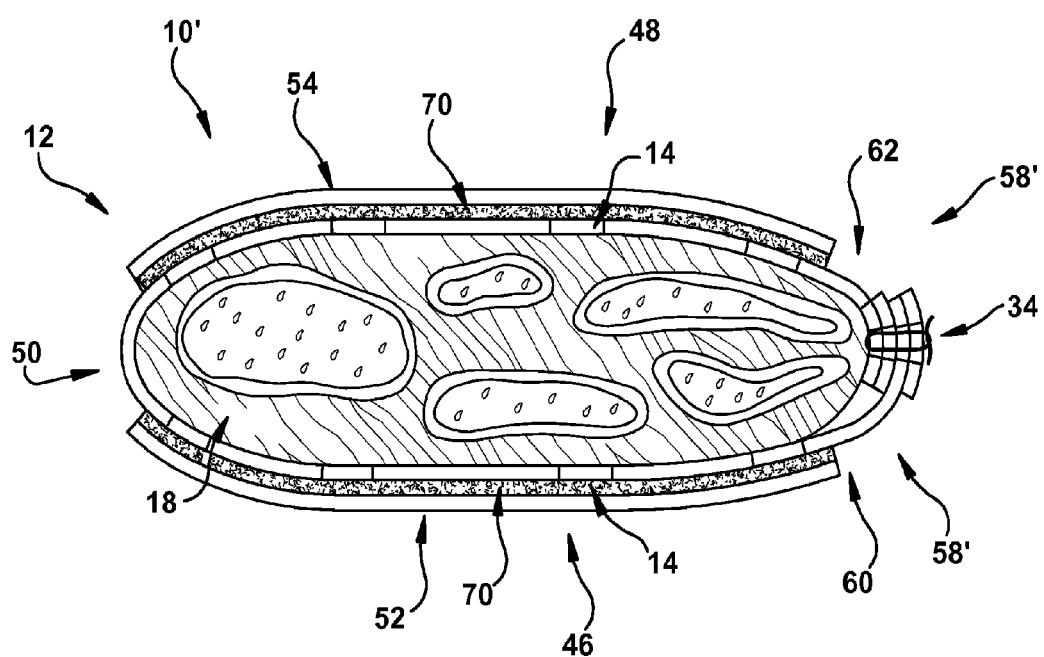
FIG. 14 is a cross-sectional view showing the implantable cuff of FIG. 13 in a closed configuration.

Another aspect of the present disclosure is illustrated in FIGS. 13-14. More particularly, FIGS. 13-14 illustrate a method for functional electrical stimulation and/or monitoring of an internal body tissue using an implantable cuff 10' that is similarly configured as the implantable cuff 10 described above. As shown in FIG. 13, for example, the implantable cuff 10' can comprise an elastic collar 12, at least one conductive segment 14 disposed on or within the elastic collar, and at least one conductor 78 in electrical communication with the at least one conductive segment. The elastic collar 12 can include first and second arm members 46 and 48, each of which has a distal end portion 58'. The first arm member 46 can have a greater overall length than the second arm member 48, which allows the distal end portions 58' to overlap with one another (discussed below). The implantable cuff 10' can further comprise a plurality of stiffening regions 70 as described above.

The implantable cuff 10' can be surgically placed around an internal body tissue, such as nerve bundle 18 (as described above). Once the implantable cuff 10' is appropriately positioned about the nerve bundle 18, the cuff is manipulated to move the cuff into the closed position. As shown in FIG. 14, for example, the second arm member 48 can be carefully folded over the uncovered portion of the nerve bundle 18 so that the second tissue contacting portion 54 covers a portion of the nerve bundle and a first inner surface 100 of the distal end portion 58' contacts the nerve bundle. Next, first arm member 46 is folded around the nerve bundle 18 so that an inner surface 102 thereof contacts an outer surface 104 of the second arm member 48. If needed, the position of the distal end portion 58' of each of the first and second arm members 46 and 48 can be adjusted so that the openings or channels 68 are aligned with one another. Once the openings or channels 68 have been aligned with each other, an attachment mechanism 34 (e.g., a suture) can be passed through each of the openings or channels and tied together to securely attach the implantable cuff 10' about the nerve bundle 18. Once the implantable cuff 10' is securely attached to the nerve bundle 18, an apparatus can be operated to deliver electrical stimulation to, and/or monitor electrical activity of, the nerve bundle (as described above).

The following examples are for the purpose of illustration only and are not intended to limit the scope of the claims, which are appended hereto.

EXAMPLE 1

A total of 12 cuffs were implanted in three cats for separate periods of 90, 84 and 88 days. The cuffs were identically constructed as the cuff 10 described and shown above, except that each of the implanted cuffs did not include any electrodes. Cuffs were implanted bilaterally on the sciatic nerves in the popliteal fossa and the median nerves just distal to the brachial plexus. Immediately after recovery from anesthesia, the cats showed no signs of pain or weakness and qualitatively had normal physiology. Throughout the implant period, the cats were monitored three times per week for any signs of pain, weakness or lameness. For the sciatic nerves, motor deficits were carefully monitored by noting any hyperextension of tarsus, knuckling, or walking on the hock of the leg, any difficulty squatting (e.g., while using a litter box), any difficulty trotting, any leg dragging or limp. Sensation involving the sciatic nerves was further monitored by testing withdrawal to foot pressure. For the median nerves, motor deficits were monitored by noting any limp or difficulty trotting, as well as by observing forelimb claw extraction and retraction as well as kneading. Sensation involving the median nerves was further monitored by testing withdrawal to pressure at the pad of the first digit of the forelimb paw.

No abnormalities or changes were observed during the implant period. Nerve conduction velocity (NCV) was measured through the region of nerve where cuffs were implanted. This was carried out at both implant and explant procedures. The NCV values were within normal limits as have been reported for cats. During explant, encapsulation was grossly noted to be minimal for cuffs on the sciatic nerves. Encapsulation around cuffs implanted on the median nerves was also small, despite the significant flexion and extension normal in the region of the implant and the more restrictive space around the electrode. Closely surrounding structures to the median nerve location include major vessels and other nerves. No deficits were noted that would indicate adverse effects on any surrounding tissue.

EXAMPLE 2

Figure 15:
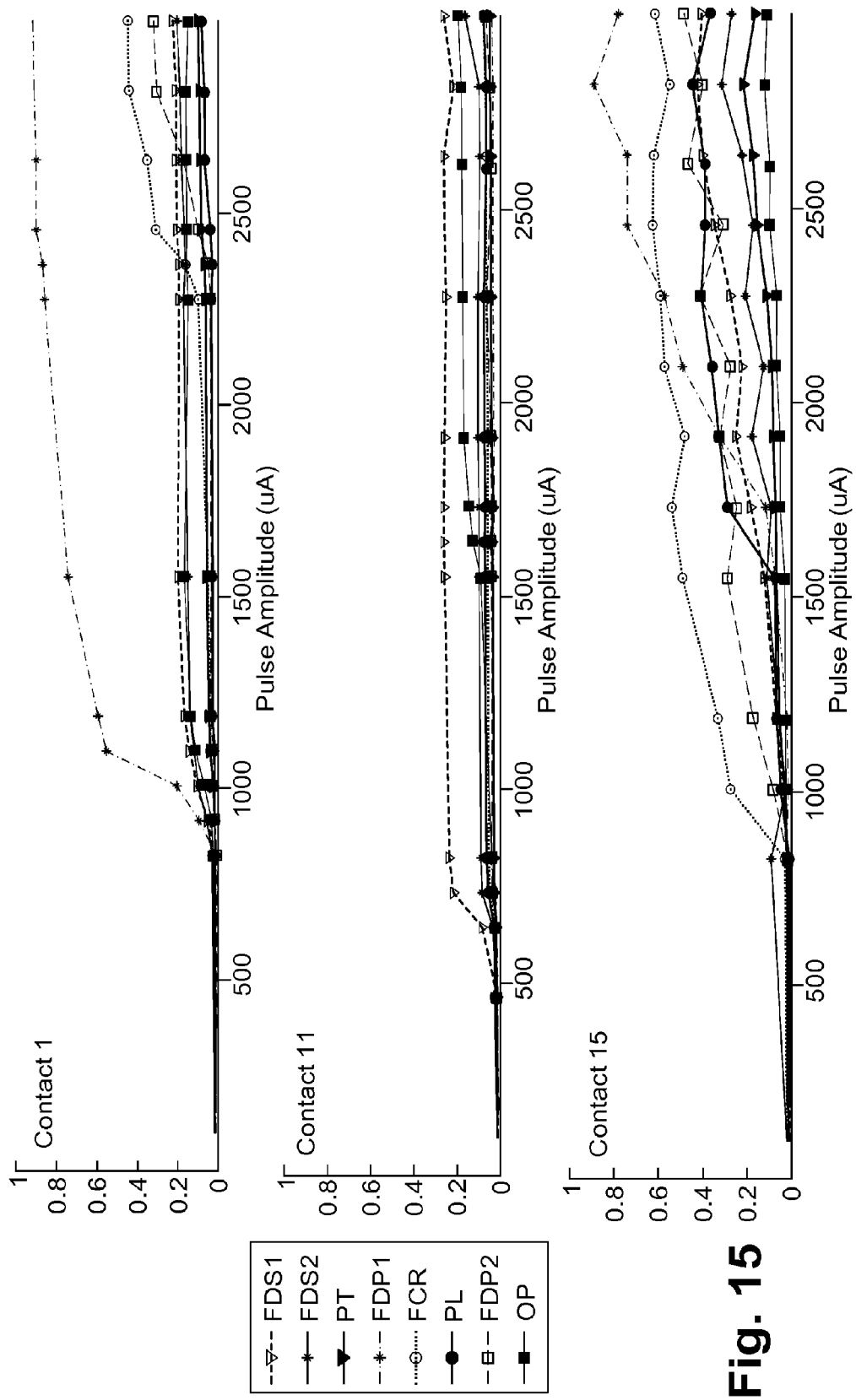
FIG. 15 is a series of recruitment curves collected from a 16-channel cuff implanted in the right median nerve at 3 months post-implant. Contacts 1, 11, and 15 selectively activated the Flexor Digitorum Superficialis, Flexor Digitorum Profundus, and the Flexor Carpi Radialis, respectively.

Cuffs identical to those in Example 1 were implanted in the upper extremity nerves of three nonhuman primates. Bipolar needle electromyography (EMG) electrodes were inserted into hand muscles innervated by the radial, median, and ulnar nerves. The EMG signals were recorded using programmable amplifiers (Tucker Davis Technologies, Alachua, Fla.). The EMG data was filtered with a low pass filter of 1000 Hz and sampled at 2.4 kHz. A 32-channel external stimulator (Tucker Davis Technologies) applied stimulation to single contacts on the nerve cuff electrode. A custom MATLAB software package controlled the data recording and the stimulator output for the pulse amplitude and pulse width. The EMG twitch response was rectified and integrated for each stimulation pulse. Recruitment curves were generated by holding either the pulse width or pulse amplitude static while the other was varied (FIG. 15). The recruitment curve of each muscle was normalized to the maximum recruitment for the given muscle. Selectivity of muscle activation was defined as the percent of activation of a particular muscle before any other muscle reached 20% activation.

Two nonhuman primates were implanted acutely with a six-channel cuff in the median, radial, and ulnar nerves. The threshold charge required to activate muscles at 10% was calculated to be 17+/−15 nC. One nonhuman primate was chronically implanted with a high density, 16-channel cuff on the ulnar nerve distal to the wrist, the median nerve distal to the elbow, and the radial nerve proximal to the elbow in the right arm for three months and in the left arm for one month. EMG electrodes were implanted in 20 muscles to measure EMG signals evoked by the stimulation. Following recovery from the implant surgery, the animal was anesthetized at weekly intervals with propofol in order to eliminate voluntary muscle activation. We recorded from a finger extensor (EDC), a thumb abductor (APL), wrist extensors (ECRB, ECRL), an elbow flexor (BR), finger flexors (FDS, FDP), wrist flexors (FCR, PL), a forearm rotator (PT), and several intrinsic hand muscles (ADM, LUM1, FDI, FPB, OP, FDMB).

Figure 16:
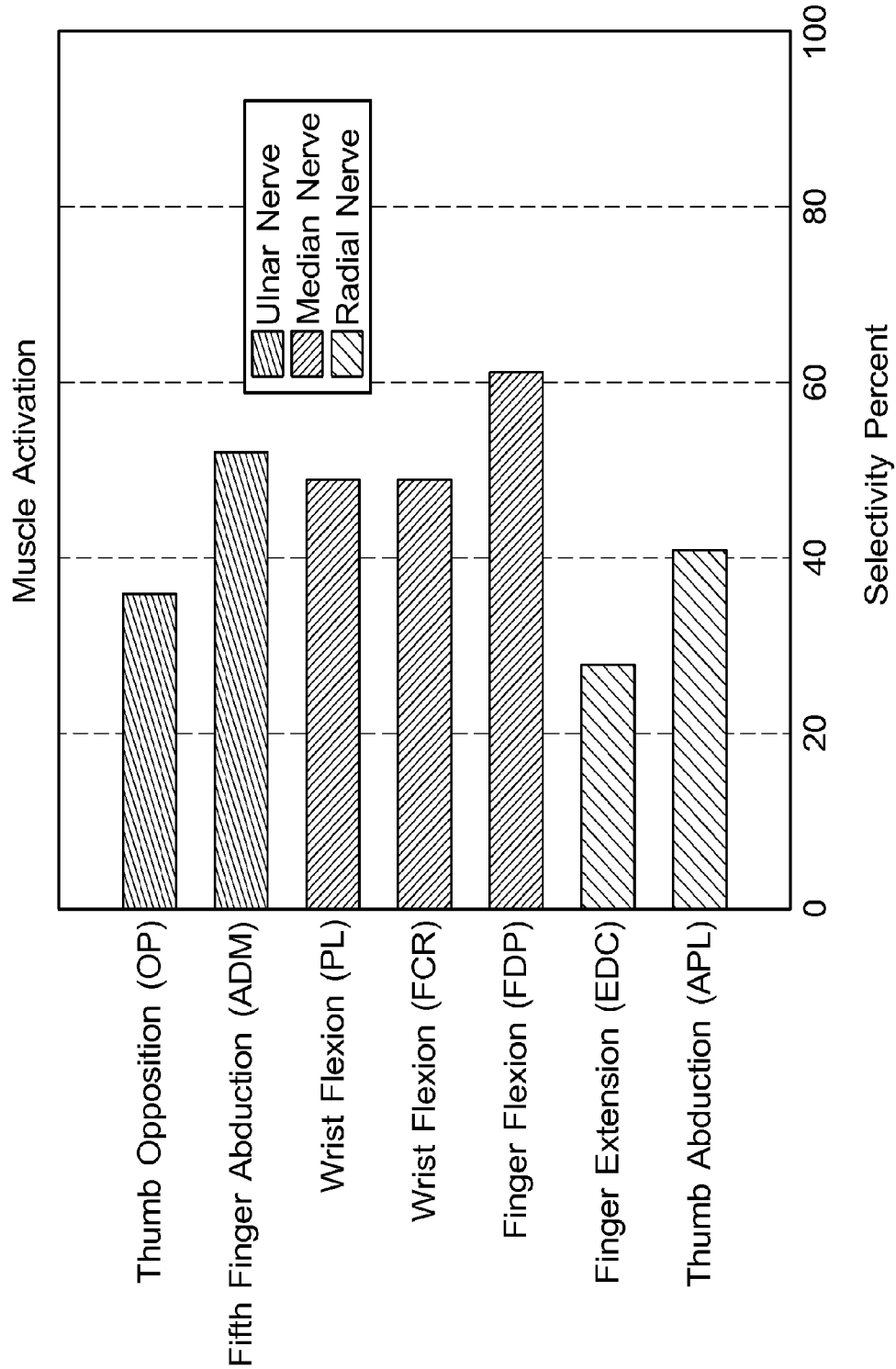
FIG. 16 is a graph showing selective functions produced through single-channel stimulation of chronically implanted cuffs in the right arm of nonhuman primates.
Figure 17:
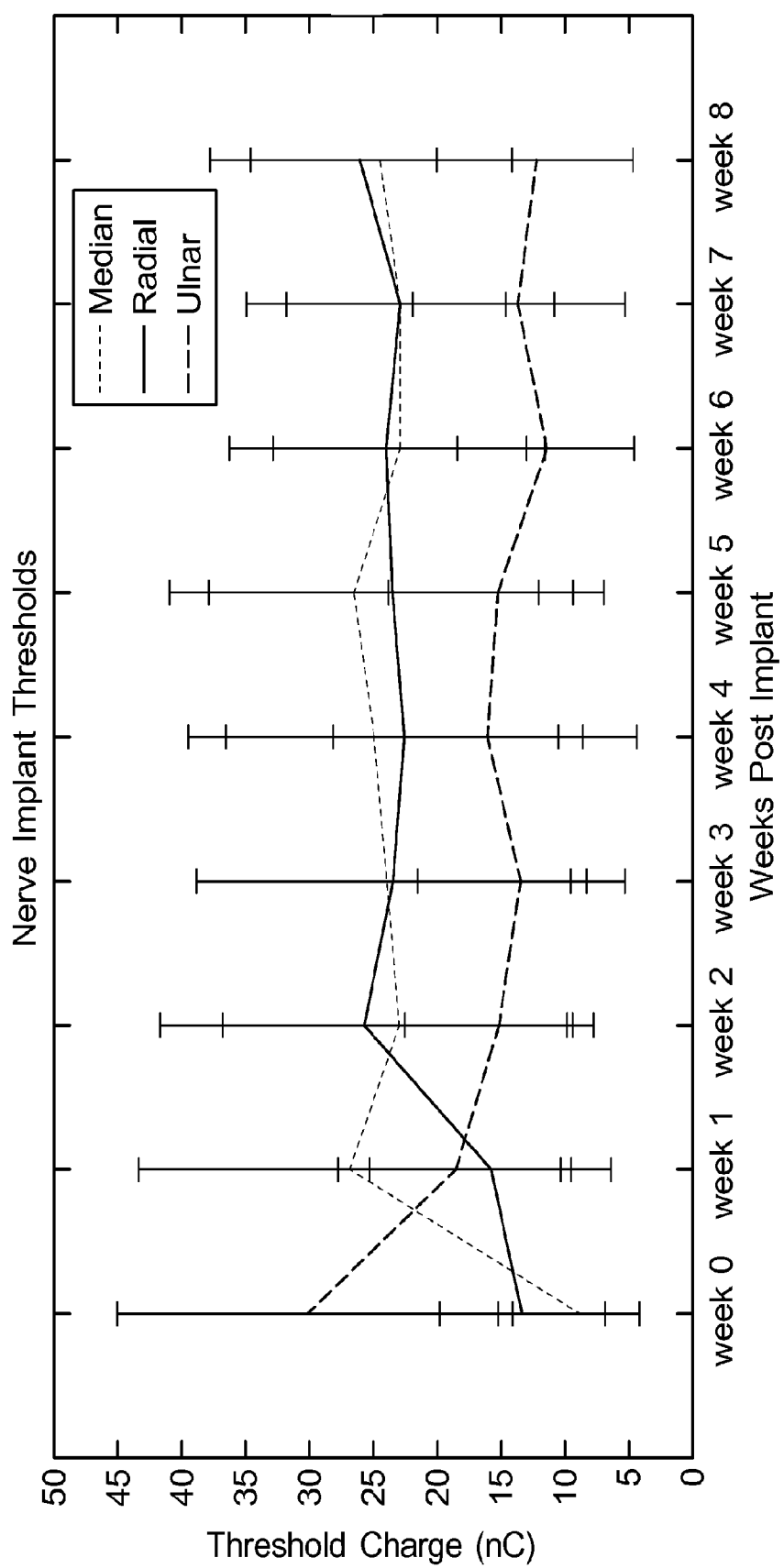
FIG. 17 is a graph showing threshold charges across all high density cuffs in the respective right arm nerves up to two-months post-implant.

All high density nerve cuff electrodes activated at least two muscles selectively in the right arm up (FIG. 16). We were able to activate thumb opposition and fifth finger abduction selectively using the ulnar nerve implant, finger and wrist flexors with the median nerve implant, and finger extensors and thumb abductor with the radial nerve implant. Thresholds stabilized 2 weeks post implant (FIG. 17). The mean stimulation charge thresholds 9 weeks after the implant were 12±8 nC, 25±10 nC, and 26±12 nC, for the ulnar, median, and radial nerve implants, respectively. High density cuffs produced stable, selective activation of seven muscles representing seven different functions critical to hand grasp in one arm.

From the above description, those skilled in the art will perceive improvements, changes and modifications. For example, it will be appreciated that one or more components of the implantable cuff 10 can be modified to become medication or fluid conductive, such as by forming fluid conduits or ducts (not shown). Such improvements, changes, and modifications are within the skill of one in the art and are intended to be covered by the appended claims.

The following is claimed:

1. An implantable cuff comprising:
an elastic collar defining an internal opening configured to receive an internal body tissue, the elastic collar comprising:
a first arm member including a first tissue contacting portion and a first bendable region, wherein the first tissue contacting portion includes a first stiffening region, wherein the first stiffening region has a stiffness that is greater than a stiffness of the first bendable region, and wherein the first bendable region has a flexibility that is greater than a flexibility of the first tissue contacting portion;
a second arm member, oppositely disposed from the first arm member, including a second tissue contacting portion and a second bendable region, wherein the second tissue contacting portion includes a second stiffening region, wherein the second stiffening region has a stiffness that is greater than a stiffness of the second bendable region, and wherein the second bendable region has a flexibility that is greater than a flexibility of the second tissue contacting portion; and
a hinge region flexibly joining the first arm member and the second arm member and spacing apart the first tissue contacting portion and the second tissue contacting portion,
wherein the first arm member and the second arm member are configured for attachment between distal end portions of the first and second arm members, and
wherein the first bendable region and the second bendable region are distal to the first stiffening region and the second stiffening region,
respectively;
at least one conductive segment disposed on or within said first tissue contacting portion and second tissue contacting portion; and
at least one conductor in electrical communication with said at least one conductive segment, said at least one conductor being configured to operably mate with an apparatus capable of delivering electrical stimulation to, and/or or recording an electrical activity of, the internal body tissue.

2. The implantable cuff of claim 1, wherein the distal ends of the first arm member and second arm member comprise one or more suture holes.

3. The implantable cuff of claim 1, wherein said elastic collar has a multi-layered configuration.

4. The implantable cuff of claim 3, wherein said elastic collar includes a first non-conductive sheet sandwiched between a backing sheet and a second non-conductive sheet.

5. The implantable cuff of claim 1, wherein the first and second stiffening regions include one or more stiffening members.

6. The implantable cuff of claim 5, wherein said one or more stiffening members has a modulus of elasticity greater than the modulus of elasticity of the first bending region and the second bending region.

7. The implantable cuff of claim 1, wherein at least one of the first and second bendable region includes a weakened section configured to tear at a pre-determined internal pressure of said elastic collar.

8. The implantable cuff of claim 1, wherein at least one of the first and second stiffening regions is configured to maintain the shape of the elastic collar while said hinge region and said first and second bendable regions impart said elastic collar with flexibility sufficient to bend about the internal body tissue.

9. A method of functional electrical stimulation and/or monitoring of an internal body tissue, said method comprising the steps of:
providing an implantable cuff, the implantable cuff including an elastic collar comprising:
a first arm member including a first tissue contacting portion and a first bendable region, wherein the first tissue contacting portion includes a first stiffening region, wherein the first stiffening region has a stiffness that is greater than a stiffness of the first bendable region, and wherein the first bendable region has a flexibility that is greater than a flexibility of the first tissue contacting portion;
a second arm member, oppositely disposed from the first arm member, including a second tissue contacting portion and a second bendable region, wherein the second tissue contacting portion includes a second stiffening region, wherein the second stiffening region has a stiffness that is greater than a stiffness of the second bendable region, and wherein the second bendable region has a flexibility that is greater than a flexibility of the second tissue contacting portion; and
a hinge region flexibly joining the first arm member and the second arm member and spacing apart the first tissue contacting portion and the second tissue contacting portion,
wherein the first arm member and the second arm member are configured for
attachment between distal end portions of the first and second arm members, and
wherein the first bendable region and the second bendable region are distal to the first stiffening region and the second stiffening region,
respectively;
wherein at least one conductive segment disposed on or within the elastic collar, and at least one conductor in electrical communication with the at least one conductive segment;
placing the implantable cuff around the internal body tissue so that a non-circumferential force is applied to the internal body tissue without damaging the tissue; and
delivering electrical stimulation to, and/or or recording an electrical activity of, the internal body tissue using the conductive segment.

10. The method of claim 9, wherein the internal body tissue is a nerve bundle or muscle filament.

11. The method of claim 10, wherein placing of the implantable cuff around the nerve bundle causes the fascicles of the nerve bundle to spread while also flattening the epineurium membrane.

12. The method of claim 11, wherein the at least one conductive segment is placed into electrical contact with one or more fascicles without penetrating the perineurium membrane of the nerve bundle.

13. The method of claim 11, wherein blood flow through the nerve bundle is not significantly decreased.

14. The method of claim 9, wherein said step of placing the implantable cuff around the internal body tissue further includes securing the distal end portion of the first arm member to the distal end portion of the second arm member using one or more sutures.

15. The method of claim 9, wherein placing of the implantable cuff around the internal body tissue results in a tapered, transverse pressure gradient to opposing surfaces of the internal body tissue.

16. The method of claim 9, further comprising releasing the implantable cuff from around the internal body tissue when a pre-determined internal pressure is exerted against a portion of the elastic collar.

17. The method of claim 9, wherein stimulation and monitoring are performed simultaneously.

18. The method of claim 9, wherein stimulation and monitoring are performed intermittently.

* * * * *

UNITED STATES PATENT AND TRADEMARK OFFICE
CERTIFICATE OF CORRECTION

PATENT NO. : 9,603,538 B2
APPLICATION NO. : 14/408011
DATED : March 28, 2017
INVENTOR(S) : Lee Fisher et al.

Page 1 of 1

It is certified that error appears in the above-identified patent and that said Letters Patent is hereby corrected as shown below:

In the Specification

In Column 1, after Line 11 insert:
--GOVERNMENT FUNDING
This work was supported, at least in part, by grant number R01-EB-001889 from The National Institutes of Health. The United States government has certain rights in this invention.--

Signed and Sealed this
Second Day of January, 2018

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

| | | |
|---|---|---|
| PATENT NO. | : 9,603,538 B2 | Page 1 of 1 |
| APPLICATION NO. | : 14/408011 | |
| DATED | : March 28, 2017 | |
| INVENTOR(S) | : Lee Fisher et al. | |

It is certified that error appears in the above-identified patent and that said Letters Patent is hereby corrected as shown below:

In the Specification

Column 1, Line 11 before the TECHNICAL FIELD heading, add the following heading:
--GOVERNMENT FUNDING
This invention was made with government support under NS074149 and EB002091 awarded by the National Institutes of Health. The government has certain rights in the invention.--

This certificate supersedes the Certificate of Correction issued January 2, 2018.

Signed and Sealed this
Seventeenth Day of June, 2025

Coke Morgan Stewart
*Acting Director of the United States Patent and Trademark Office*